United States Patent [19]

Lee et al.

[11] Patent Number: 5,625,706
[45] Date of Patent: Apr. 29, 1997

[54] METHOD AND APPARATUS FOR CONTINOUSLY MONITORING AND FORECASTING SLIDE AND SPECIMEN PREPARATION FOR A BIOLOGICAL SPECIMEN POPULATION

[75] Inventors: Shih-Jong J. Lee, Bellevue; Dayle G. Ellison, Redmond; Paul S. Wilhelm, Kirkland, all of Wash.

[73] Assignee: NeoPath, Inc., Redmond, Wash.

[21] Appl. No.: 455,296

[22] Filed: May 31, 1995

[51] Int. Cl.[6] ............................................. G06K 9/00
[52] U.S. Cl. ............................................. 382/128; 382/133
[58] Field of Search ............................. 382/128, 133, 382/134, 129; 356/39, 42

[56] References Cited

U.S. PATENT DOCUMENTS

| | | | |
|---|---|---|---|
| 3,824,393 | 7/1974 | Brain | 356/39 |
| 4,034,342 | 7/1977 | Kruklitis | 340/146.3 |
| 4,085,006 | 4/1978 | Mindick et al. | 195/103.7 |
| 4,175,860 | 11/1979 | Bacus | 356/39 |
| 4,637,053 | 1/1987 | Schalkowsky | 382/133 |
| 4,812,412 | 3/1989 | Turner | 436/15 |
| 4,839,194 | 6/1989 | Malluche et al. | 427/2 |
| 4,965,725 | 10/1990 | Rutenberg | 364/413.1 |
| 5,029,226 | 7/1991 | Klein et al. | 382/50 |
| 5,072,382 | 12/1991 | Kamentsky | 364/413.08 |
| 5,139,031 | 8/1992 | Guirguis | 128/771 |
| 5,235,522 | 8/1993 | Bacus | 356/39 |
| 5,257,182 | 10/1993 | Luck et al. | 382/36 |
| 5,287,272 | 2/1994 | Rutenberg et al. | 364/413.01 |
| 5,315,700 | 5/1994 | Johnston et al. | 345/163 |
| 5,357,977 | 10/1994 | Michels | 128/758 |
| 5,361,140 | 11/1994 | Hayenga et al. | 358/446 |
| 5,428,690 | 6/1995 | Bacus et al. | 382/128 |
| 5,449,622 | 9/1995 | Yabe et al. | 356/39 |
| 5,488,469 | 1/1996 | Yamamoto et al. | 356/39 |

OTHER PUBLICATIONS

Bacus, James W. and Les J. Grace, "Optical Microscope System For Standardized Cell Measurements and Analyses", *Applied Optics*, 26:16, pp. 3280–3293, 15 Aug. 1987.

Bartels, Peter H., et al., "A Self–Learning Computer Program for Cell Recognition", *ACTA Cytologica: The Journal of Clinical Cytology*, 14:8, pp. 486–494, Oct. 1970.

Tanaka, Noboru, et al., "Automated Cytologic Screening System (CYBEST Model 4): an Integrated Image Cytometry System", Reprinted from *Applied Optics*, vol. 26, No. 16, pp. 3301–3307, Aug. 15, 1987. Copyright© 1987 by the Optical Society of America and reprinted by permission of the copyright owner.

(List continued on next page.)

*Primary Examiner*—Leo Boudreau
*Assistant Examiner*—Bhavesh Mehta
*Attorney, Agent, or Firm*—Leone & Moffa, P.A.

[57] ABSTRACT

An automated laboratory process monitoring method for a computer controlled automated cytology system initializes lab process assessment slide data so as to produce an initial batch of qualified slides. Monitor parameters are extracted from the initial batch of qualified slides so as to determine control limits. Field data is monitored by comparing the field data to the control limits.

33 Claims, 15 Drawing Sheets

OTHER PUBLICATIONS

Duda, Richard O. and Peter E. Hart, "Fisher's Linear Discriminant", *Patent Classification and Scene Analysis*, Copyright ©1973, pp. 114–119.

Dytch, Harvey E. et al., "An Interactive Microcomputer-–Based System for the Quantitative Analysis of Stratified Tissue Sections", *Analytical and Quantitative Cytology and Histology*, vol. 9, No. 1, pp. 69–78, Mar. 1987.

Enslein, Kurt and Peter W. Neurath, "Augmented Stepwise Discriminant Analysis Applied to Two Classification Problems in the Biomedical Field", *Computers and Biomedical Research*, 2, 568–581 (1969).

Kurman, Robert J. et al., "Part 1: Specimen Adequacy" and Part 2: Descriptive Diagnoses, *The Bethesda System for Reporting Cervical/Vaginal Cytologic Diagnoses*, © 1994 Springer–Verlag, pp. 1–81.

Smith, Warren J., "Modern Optical Engineering: The Design of Optical Systems", Copyright ©1966 by McGraw–Hill Book Company, pp. 308–325.

Weber, J.E. et al., "Fuzzy Reasoning, Possibility Theory and Probality Theory in Expert Systems for Histopathology", IEEE/Ninth Annual Conference of the Engineering in Medicine and Biology Society, pp. 1560–1561, ©1987.

Wied, G.L. et al., "Expert Systems as Classifiers in Diagnostic Cytopathology", IEEE/Ninth Annual Conference of the Engineering in Medicine and Biology Society, pp. 1915–1917, ©1987.

Wied, G.L. et al., "Expert System Design Under Uncertainty of Human Diagnosticians", IEEE/Eighth Annual Conference of the Engineering in Medicine and Biology Society, pp. 757–760, ©1986.

Wied, G.L. et al., "Ticas–Stratex, an Expert Diagnostic System For Stratified Cervical Epithelium", IEEE/Ninth Annual Conference of the Engineering in Medicine and Biology Society, pp. 1557–1559, ©1987.

Serra, J., *Image Analysis and Mathematical Morphology*, pp. 372–423, Academic Press, 1982.

Patten, Jr., Stanley, "Diagnostic Cytopathology of the Uterine Cervix", Basel, Switzerland, Publisher: S. Karger, 1969, 2nd Edition 1978, Third volume in *Monographs in Clinical Cytology*, edited by G.L. Wied, pp. 10–15.

Patten, Jr., Stanley, "Diagnostic Cytopathology of the Uterine Cervix", Basel, Switzerland, Publisher: S. Karger, 1969, 2nd Edition 1978, Third volume in *Monographs in Clinical Cytology*, edited by G.L. Wied, pp. 1–9.

Patten, Jr., Stanley, "The Automation of Uterine Cancer Cytology", *Sensitivity and Specificity of Routine Diagnostic Cytology*, Tutorials of Cytology,Chicago, IL, 1976, edited by Wied, Bahr and Bartels, pp. 406–419.

Lundsteen, C., et al., Abstract from *Clin Genet.*, Department of Obstetrics and Gynecology, Rigshospitalet, Copenhagen, Denmark, vol. 45, No. 2, Feb. 1994, pp. 62–66.

Kaplow, L.S., Abstract from *Histochem Cytochem.*, vol. 25, No. 8, Aug. 1977, pp. 990–1000.

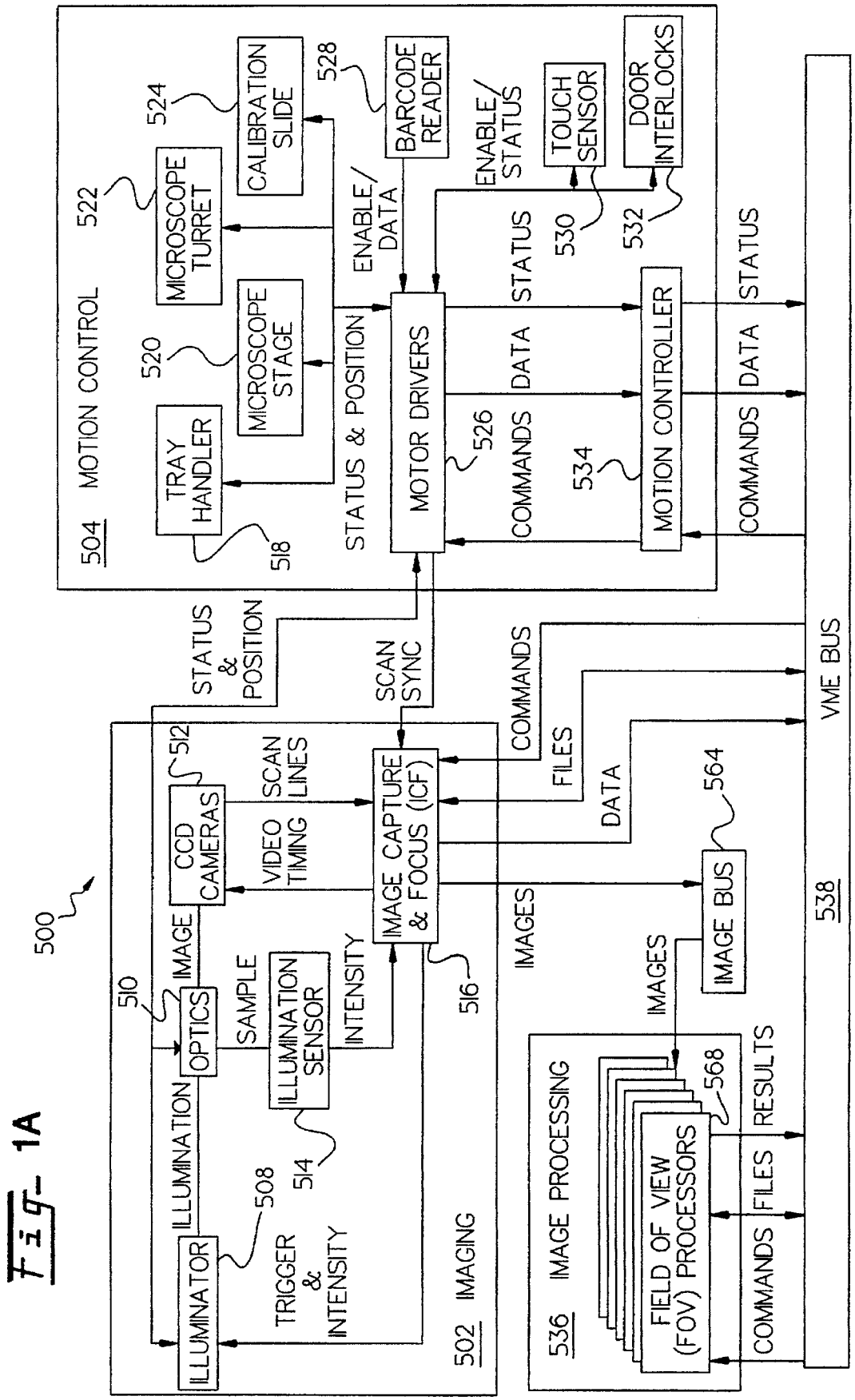

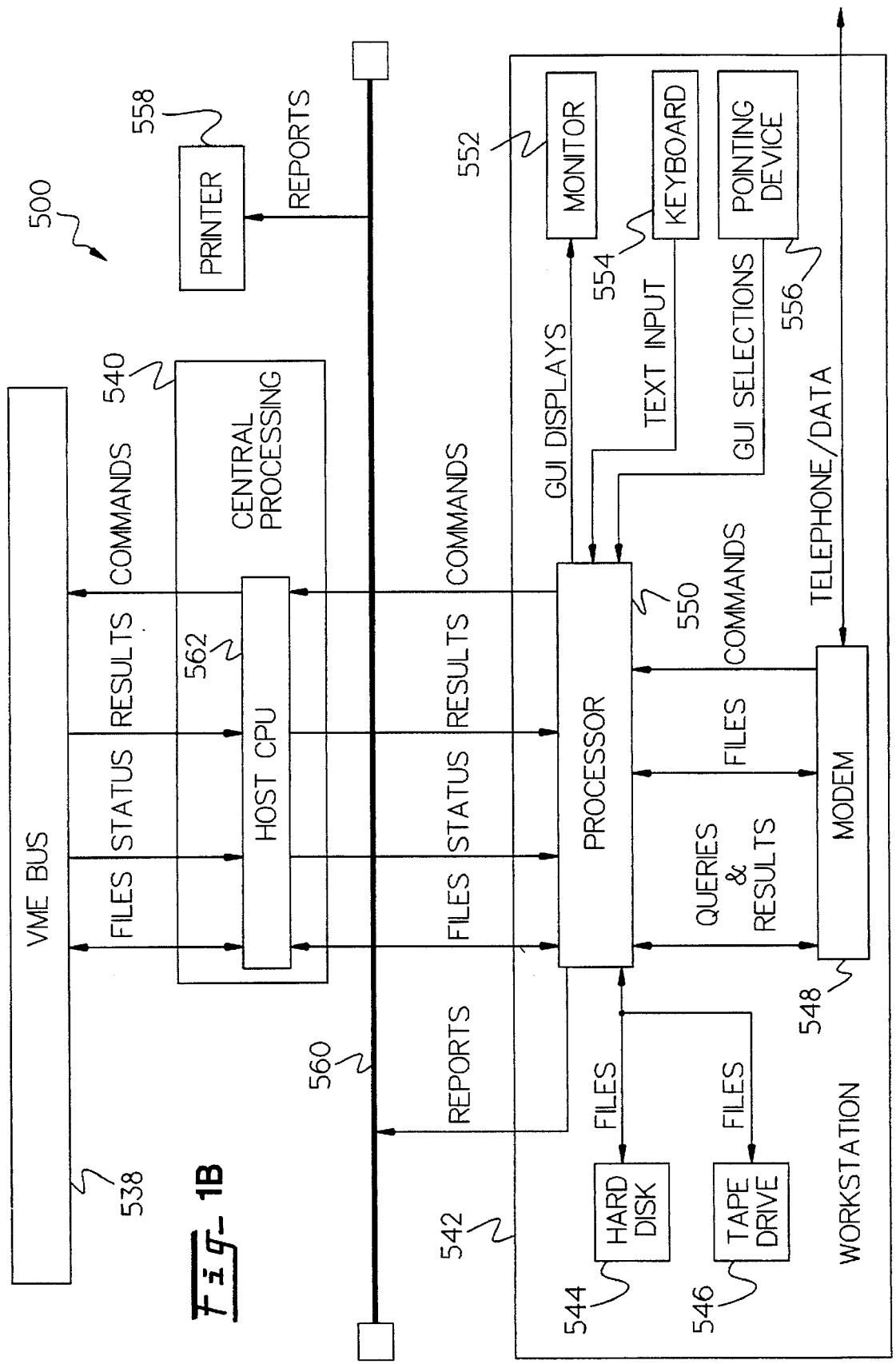

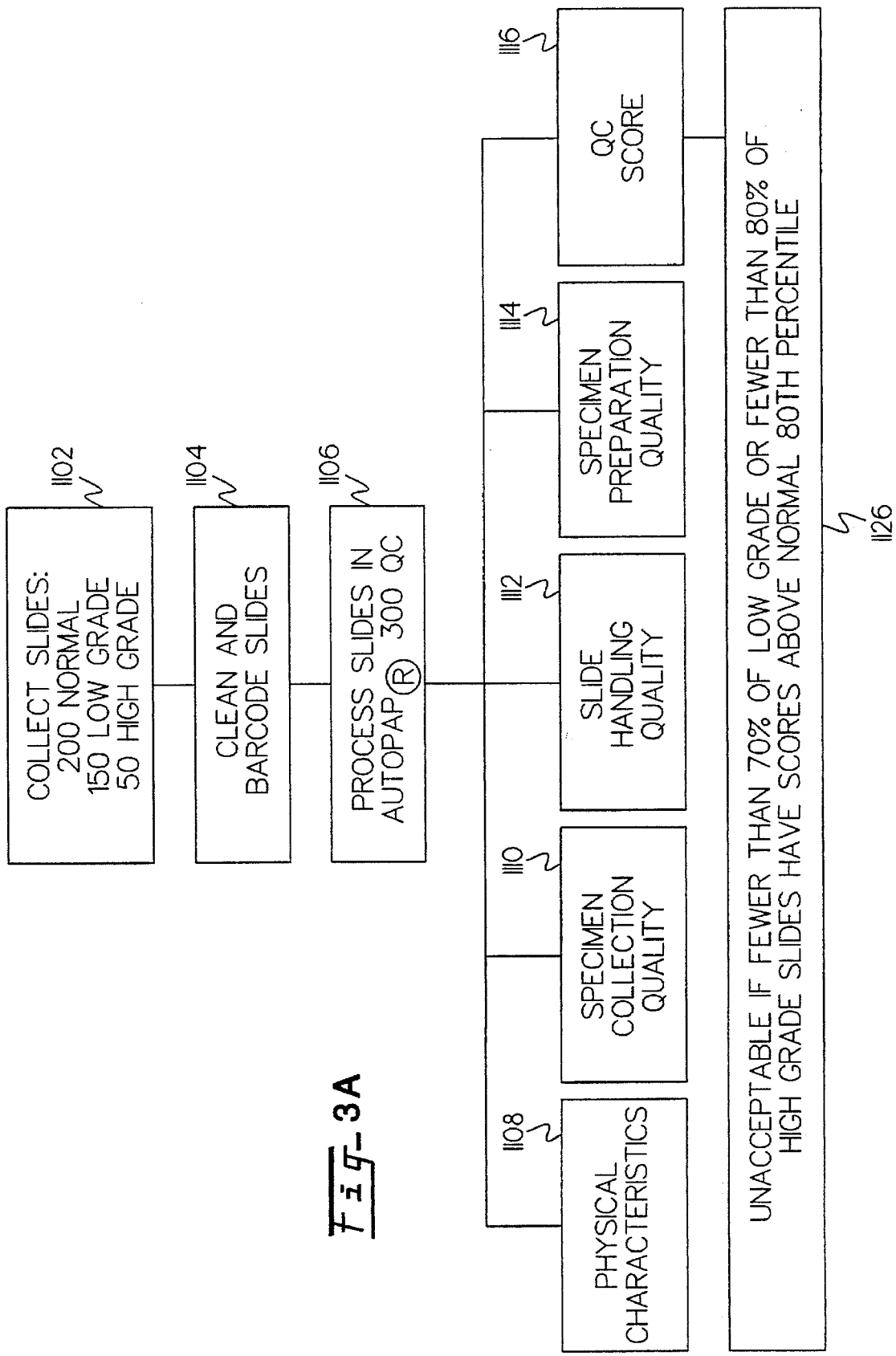

METHOD AND APPARATUS FOR CONTINOUSLY MONITORING AND FORECASTING SLIDE AND SPECIMEN PREPARATION FOR A BIOLOGICAL SPECIMEN POPULATION

BACKGROUND OF THE INVENTION

This invention relates generally to automated cytological analysis systems and, more particularly, to a method and apparatus for continuous automatic monitoring and forecasting of slide and specimen preparation quality for biological specimen fixed and stained on glass slides.

Detection of disease processes is dependent on adequate specimen collection, proper fixation, staining and mounting of specimens on microscope slides. Laboratory preparation processes can vary over time because variations may occur in specimen collection, fixation, staining and mounting quality for a population of slide specimens. To ensure that slides and specimens are continuously prepared in a fashion which allows for the detection of disease processes, continuous monitoring and forecasting of slide and specimen preparation quality is required.

Standards for the practice of cervical/vaginal cytology have been suggested by the introduction of the well known Bethesda System. However, significant variations in cytological specimens such as, for example, specimens stained with the well known Papanicolaou stain ("pap smears") still occur. Although the pap smear screening process can accommodate slide population, sampling, and preparation variations to some degree, variations that adversely affect the screener's ability to detect the disease process can occur. It is, therefore, important to develop a monitoring process to detect and forecast such variations in order to maintain adequate laboratory preparation for the detection of disease process.

Specimen preparation is monitored periodically by human visual review. This solution has not been satisfactory because the periodic monitoring process is subjective and could suffer from period to period and reviewer to reviewer inconsistency. Also, if a laboratory process is found unsatisfactory with periodic monitoring, it may not be possible or desirable to retrospectively re-process those slides processed during the unsatisfactory period. No alternative solution has been available prior to this invention.

It is one motivation of the invention to automate a process that is currently carried out using subjective manual processes. It is another motivation of the invention to improve the quality and consistency of smear and slide preparation for the detection of disease processes.

In contrast to the prior art, the present invention provides a method and apparatus wherein slides and specimens are examined in an automated biological specimen screener such as the AutoPap 300 System made by NeoPath, Inc. of Redmond, Wash., U.S.A. The automated biological specimen screener measures, among other things, parameters of specimen collection quality, fixation quality, staining quality and mounting quality. These measures are objective and provide a consistent standard of evaluation. Rather than monitor periodically, an automated biological specimen screener made in accordance with the present invention measures a consistently updated most recent set of slides as part of the monitoring process. Continuous monitoring of process parameters provides the means to administer a short term and mid-term process tracking mechanism. The short-term tracking mechanism reports recent (that is, relative to mid-term) variations in the laboratory process that can be adjusted before adverse screening conditions occur. It also allows the laboratory to track variation patterns, providing the means to forecast adverse conditions which can occur if the parameters of the mid-term tracking mechanism fall outside acceptable limits. For example, keyed by slides which are increasingly borderline acceptable for the detection of disease processes, short-term tracking allows a laboratory to immediately detect changes in nuclear staining. These changes suggest the need to adjust staining solutions. The staining parameters for the short term tracking can be used to adjust a staining process in an automated fashion, before staining quality becomes unacceptable.

SUMMARY OF THE INVENTION

An automated laboratory process monitoring method for a computer controlled automated cytology system initializes lab process assessment slide data so as to produce an initial batch of qualified slides. Monitor parameters are extracted from the initial batch of qualified slides so as to determine control limits. Field data is monitored by comparing the field data to the control limits.

The method and apparatus of the invention uses objective measures rather than subjective measures, monitors continuously rather than periodically, and provides a mechanism for forecasting slide and specimen preparation variations which result in inadequate specimen collection, proper fixation, staining and mounting of specimen before the qualities become unacceptable.

Other objects, features and advantages of the present invention will become apparent to those skilled in the art through the description of the preferred embodiment, claims and drawings herein wherein like numerals refer to like elements.

BRIEF DESCRIPTION OF THE DRAWINGS

To illustrate this invention, a preferred embodiment will be described herein with reference to the accompanying drawings.

FIGS. 1A, 1B and 1C show one embodiment of the invention.

FIGS. 3A, 3B, 3C, 3D and 3E are more detailed flow charts of a method for assessing slide and specimen preparation quality.

DETAILED DESCRIPTION OF THE PREFERRED EMBODIMENT

Figure 1C:
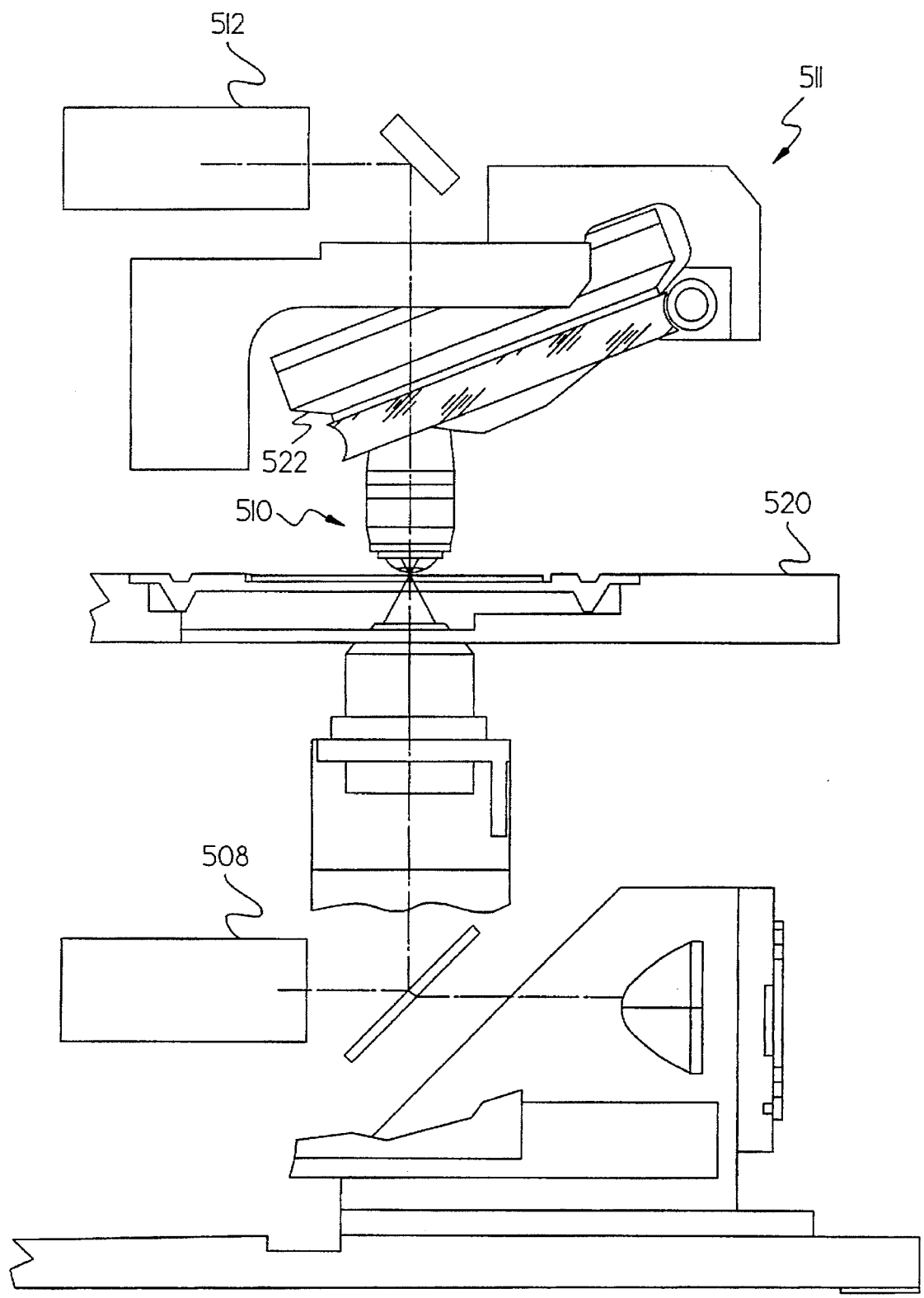

The present invention provides a method for continuous monitoring and forecasting of a clinical laboratory's slide and specimen preparation quality for biological specimen. In a presently preferred embodiment of the invention, the invention is applied to use of the AutoPap 300 system, an automated Pap smear screener, in the laboratory setting.

The invention provides a set of procedures, herein called Laboratory Process Monitoring, that a clinical laboratory can use to monitor and forecast slide and specimen preparation quality for biological specimen fixed and stained on glass slides. Laboratory preparation processes may vary over time with variations in specimen collection, fixation, staining and mounting quality for a population of slide specimen. The Laboratory Process Monitoring procedures specifically measure, test, and provide short- and mid-term tracking capabilities to the laboratory for slide physical characteristics, specimen collection quality, slide handling quality and preparation quality. The short term tracking capability allows a laboratory to adjust process before adverse conditions, which can lead to reduced detection of disease processes, occur.

In a presently preferred embodiment of the invention, the system disclosed herein is used in a system for analyzing cervical pap smears, such as that shown and disclosed in U.S. patent application Ser. No. 07/838,064, entitled "Method For Identifying Normal Biomedical Specimens", by Alan C. Nelson, et al., filed Feb. 18, 1992; U.S. patent application Ser. No. 08/179,812 filed Jan. 10, 1994, now U.S. Pat. No. 0,528.703 which is a continuation in part of abandoned U.S. patent application Ser. No. 07/838,395, entitled "Method For Identifying Objects Using Data Processing Techniques", by S. James Lee, et al., filed Feb. 18, 1992; U.S. patent application Ser. No. 07/838,070, now U.S. Pat. No. 5,315,700, entitled "Method And Apparatus For Rapidly Processing Data Sequences", by Richard S. Johnston et al., filed Feb. 18, 1992; U.S. patent application Ser. No. 07/838,065, now U.S. Pat. No. 5,361,140 entitled "Method and Apparatus for Dynamic Correction of Microscopic Image Signals" by Jon W. Hayenga et al., filed Feb. 18, 1992; and U.S. patent application Ser. No. 08/302,355, filed Sep. 7, 1994 entitled "Method and Apparatus for Rapid Capture of Focused Microscopic Images" to Hayenga et al., which is a continuation-in-part of abandoned application Ser. No. 07/838,063 filed on Feb. 18, 1992 the disclosures of which are incorporated herein, in their entirety, by the foregoing references thereto.

The present invention is also related to biological and cytological systems as described in the following patent applications which are assigned to the same assignee as the present invention, filed on Sep. 20, 1994 (unless otherwise noted), and which are all hereby incorporated by reference including U.S. patent application Ser. No. 08/309,118 to Kuan et al. entitled, "Field Prioritization Apparatus and Method," U.S. patent application Ser. No. 08/309,061 to Wilhelm et al., entitled "Apparatus for Automated Identification of Cell Groupings on a Biological Specimen," U.S. patent application Ser. No. 08/309,116 to Meyer et al. entitled "Apparatus for Automated Identification of Thick Cell Groupings on a Biological Specimen," U.S. patent application Ser. No. 08/098,115 to Lee et al. entitled "Biological Analysis System Self Calibration Apparatus," U.S. patent application Ser. No. 08/308,992 to Lee et al. entitled "Apparatus for Identification and Integration of Multiple Cell Patterns," U.S. patent application Ser. No. 08/309,063 to Lee et al. entitled "A Method for Cytological System Dynamic Normalization," U.S. patent application Ser. No. 08/309,248 to Rosenlof et al. entitled "Method and Apparatus for Detecting a Microscope Slide Coverslip," U.S. patent application Ser. No. 08/309,077 to Rosenlof et al. entitled "Apparatus for Detecting Bubbles in Coverslip Adhesive," U.S. patent application Ser. No. 08/309,931 to Lee et al. entitled "Cytological Slide Scoring Apparatus," U.S. patent application Ser. No. 08/309,148 to Lee et al. entitled "Method and Apparatus for Image Plane Modulation Pattern Recognition", U.S. patent application Ser. No. 08/309,250 to Lee et al. entitled "Apparatus for the Identification of Free-Lying Cells," U.S. patent application Ser. No. 08/309,117 to Wilhelm et al., entitled "Method and Apparatus for Detection of Unsuitable Conditions for Automated Cytology Scoring."

Now refer to FIGS. 1A, 1B and 1C which show a schematic diagram of one embodiment of the apparatus of the invention 500. The apparatus of the invention comprises an imaging system 502, a motion control system 504, an image processing system 536, a central processing system 540, and a workstation 542. The imaging system 502 is comprised of an illuminator 508, imaging optics 510, a CCD camera 512, an illumination sensor 514 and an image capture and focus system 516. The image capture and focus system 516 provides video timing data to the CCD cameras 512, the CCD cameras 512 provide images comprising scan lines to the image capture and focus system 516. An illumination sensor intensity is provided to the image capture and focus system 516 where an illumination sensor 514 receives the sample of the image from the optics 510. In some embodiments optics 510 may comprise color filters. In one embodiment of the invention, the optics may further comprise an automated microscope 511. The illuminator 508 provides illumination of a slide. The image capture and focus system 516 provides data to a VME bus 538. The VME bus distributes the data to an image processing system 536. The image processing system 536 is comprised of field-of-view processors 568. The images are sent along the image bus 564 from the image capture and focus system 516. A central processor 540 controls the operation of the invention through the VME bus 538. In one embodiment the central processor 562 comprises a MOTOROLA 68030 CPU. The motion controller 504 is comprised of a tray handler 518, a microscope stage controller 520, microscope tray controller 522, and a calibration slide 524. The motor drivers 526 position the slide under the optics. A bar code reader 528 reads a barcode located on the slide 524. A touch sensor 530 determines whether a slide is under the microscope objectives, and a door interlock 532 prevents operation in case the doors are open. Motion controller 534 controls the motor drivers 526 in response to the central processor 540. An Ethernet communication system 560 communicates to a workstation 542 to provide control of the system. A hard disk 544 is controlled by processor 550. In one embodiment, processor 550 may comprise a workstation. A tape drive 546 is connected to the processor 550 as well as a modem 548, a monitor 552, a keyboard 554, and a mouse pointing device 556. A printer 558 is connected to the ethernet 560.

During operation, the central computer 540, running a real time operating system, controls the microscope 511 and the processor to acquire and digitize images from the microscope 511. The flatness of the slide may be checked, for example, by contacting the four corners of the slide using a computer controlled touch sensor. The computer 540 also controls the microscope 511 stage to position the specimen under the microscope objective, and from one to fifteen field of view (FOV) processors 568 which receive images under control of the computer 540.

It is to be understood that the various processes described herein may be implemented in software suitable for running on a digital processor. The software may be embedded, for example, in the central processor 540.

Laboratory Process Assessment Slide Data

Figure 2:
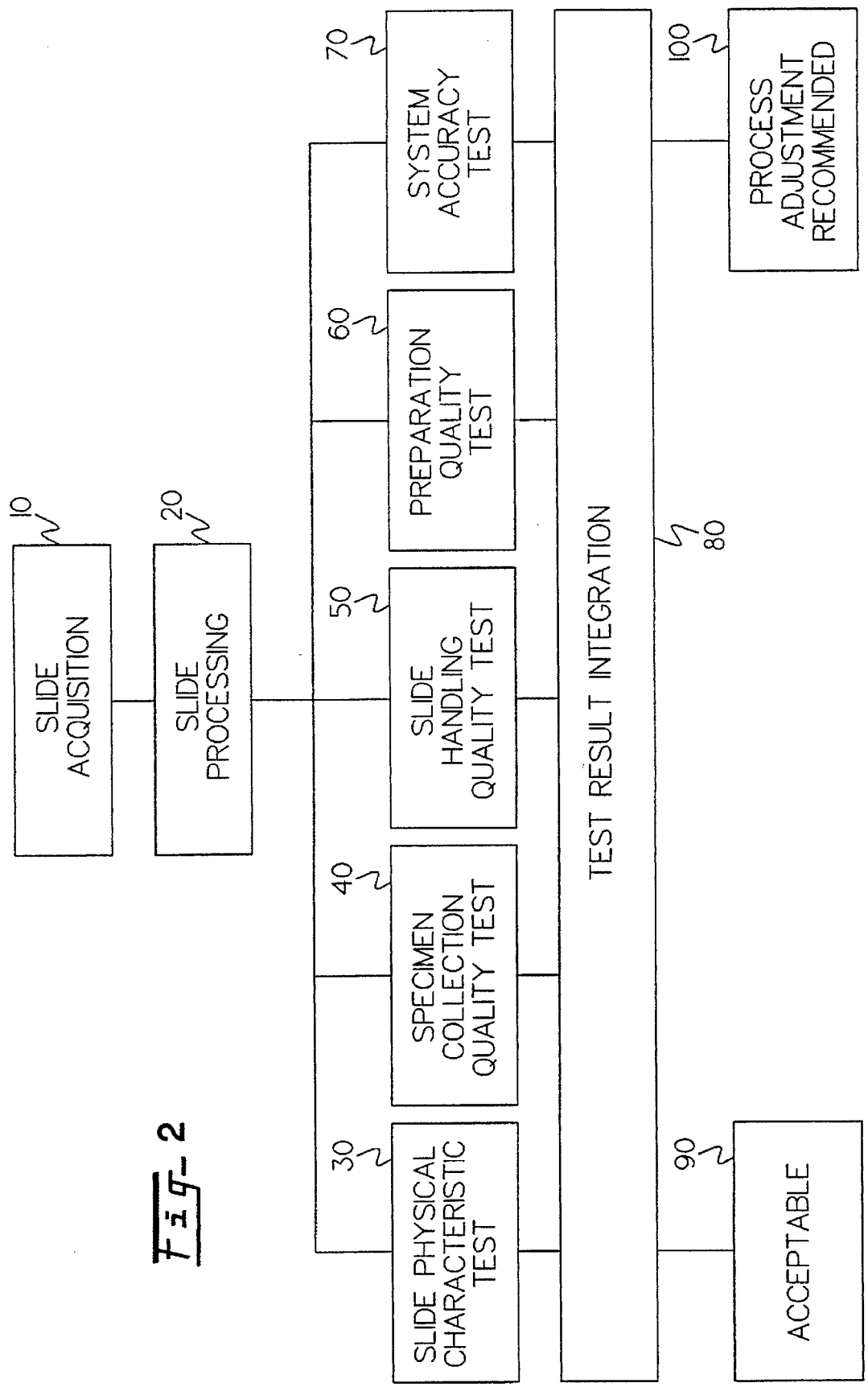
FIG. 2 shows a flow chart of a method for assessing slide and specimen preparation quality.

Refer now to FIG. 2 which shows a process flow diagram of a method for assessing slide and specimen preparation quality in accordance with the laboratory process assessment of slides employed in the invention. A technician gathers a set of laboratory slides with representative normal and abnormal slides in step 10. The slides may all be from a laboratory chosen to be evaluated. In the preferred embodiment, the assessor acquires 400 slides from the laboratory. The slide set consists of the following slides:

200 within normal limit slides,
150 low grade SIL slides, and
50 high grade SIL slides.

Low grade squamous intraephithelial lesions (LSIL) and high grade SIL (HSIL) are low grade and high grade squamous intraephithelial lesions. These lesions are the extremes of a spectrum of lesions which may include noninvasive cervical epithelial abnormalities traditionally classified as flat condyloma, dysplasia/carcinoma in situ, and cervical intraepithelial neoplasia.

An automated system, such as, for example, is described in the referenced patents, processes the slide set to obtain data for assessing slide and specimen preparation quality in step 20. In one preferred embodiment, the automated system may comprise the AutoPap® 300, available from NeoPath, Inc. Slides are stained and coverslips are applied. The automated system processes and obtains data from the acquired slides.

During processing of a slide by the automated system, a slide's processing results may fall outside established processing limits. Slide processing failures for which successful setup is not attained, are referred to as slide scanning or set-up failures. Some slides may be set up successfully during processing but have other characteristics such as certain preparation related characteristics, that prevent successful processing by the automated system. Processing failures may thereby result. Such failures are referred to as process suitability failures.

In steps 30–70, the automated system performs a series of tests on the data obtained in step 20. In step 30, the automated system performs a Slide Physical Characteristics Test to evaluates the physical characteristics of Pap Smear slides to determine if they may be successfully set up and scanned by a predetermined automated biological specimen analyzer, such as the AutoPap® 300 System. The Slide Physical Characteristics Test evaluates the physical characteristics of the slides acquired from the laboratory. These physical characteristics may include, for example, the characteristics shown in Table 1.

TABLE 1

Slide too thick
Unable to map coverslip surface
Coverslip edges not detected
Coverslip length not 40, 50, or 60 mm
Coverslip width not with limits TABLE 1-continued Coverslip corners not square
Coverslipped area too small
Coverslip skewed on slide
Unable to focus on specimen
Coverslip and specimen too thin
Coverslip and specimen too thick During evaluation, the automated system discontinues processing for slides that fall outside of an acceptable range for any of the preselected criteria. The automated system may count a proportion of slides failing processing. In one preferred embodiment, the slide set is considered to pass if the proportion of slides failing processing is less than 6%; otherwise the slide set fails.

In step 40, the automated system performs a Specimen Collection Quality Test to evaluate the quality and sufficiency of the specimen material sampled on the slide. Specimen collection quality is highly dependent upon a clinic's sampling tools and techniques for specimen collection. In the preferred embodiment, the Specimen Collection Quality Test may comprise two tests. Tables 2 and 3 list qualities for which the slide set may be tested. Slides failing these tests comprise the specimen collection quality failures. Table 2 tabulates slide set-up related failures. Table 3 tabulates failures related to process suitability failures. Process suitability failures may include, for example, slides that are set up successfully but for which process results cannot be expected to be reliable, for example, when the process detect too few reference cells. The proportion of slides failing processing for these reasons is measured. In the preferred embodiment, if the proportion of slides that failed the first test is less than 7%, the slide set is considered to pass the first test; otherwise, the slide set fails.

In the preferred embodiment, the second specimen quality test measures and ranks the reference cell ratio for all normal slides that are successfully processed. The reference cell ratio is the number of detected reference cells (that is, free-lying intermediate cells) on a slide divided by the number of all objects detected on the slide. In one preferred embodiment, if 85% of the normal slides have a reference cell ratio greater than 0.015, then the slide set is considered to pass the test; otherwise, the slide set fails.

The slide set is required to pass both specimen quality tests to pass the Specimen Collection Quality Test.

TABLE 2

Lack of material in center
Too few points for low-power focus map
Specimen distributed in small area
Unable to focus on specimen
Specimen tilt
Too few fields ranked in low-power scan
Too few points for high-power focus map
High-power focus surface too variable
Too few focused fields in high-power scan

TABLE 3

Insufficient reference cells
Image quality not within limits, percentage of fields focused on first try.
Image quality not within limits, percentage of fields never focused.

The automated system performs a Slide Handling Quality Test in step 50. The Slide Handling Quality Test determines if slide handling practices may need to be modified to facilitate effective processing on a selected automated system, such as the AutoPap® 300 System. The test evaluates the quality of slide barcoding, cleaning, and loading practices at a preselected clinical site. Tables 4 and 5 list tests-for slide handling quality failures. Table 4 tabulates slide set-up related failures. Table 5 tabulates failures related to process suitability failures. The system measures the proportion of slides failing these tests. In the preferred embodiment, if the proportion of slides that failed is less than 5%, the slide set is considered to pass the slide handling quality test; otherwise, the slide set fails.

TABLE 4

Slide barcode not read
Slide tilted

TABLE 5

Image quality not within limits, excessive striping.
Image quality not within limits, high power magnification image saturation (small amounts)
Image quality not within limits, high power magnification image saturation (large amounts)
Image quality not within limits, low power magnification image saturation.

The automated system performs a Preparation Quality Test in step 60. The Preparation Quality Test evaluates the result of laboratory fixation, staining, and coverslipping processes to determine whether the presentation of cells is within an acceptable range. In the preferred embodiment, five tests comprise preparation quality test—to pass the full test, the slide set must pass all tests. Referring to Tables 6 and 7, slides which fail processing for the tabulated reasons comprise the preparation quality failures. The proportion of slides failing processing for these reasons is measured. Table 6 tabulates slide set-up related failures. Table 7 tabulates failures related to process suitability failures. In the preferred embodiment, if the proportion of slides that failed the first test is less than 5%, the slide set passes the first test; otherwise, the slide set fails.

TABLE 6

Too many bubbles
Too few fields ranked in low-power scan

TABLE 7

Stain average not within limits
Cytoplasm Staining not within limits
Staining detail not within limits
Nuclear/Cytoplasm contrast not within limits
Insufficient reference cells
Image quality not within limits, high power magnification image saturation (large amounts)
Image quality not within limits, low power magnification image saturation.

In the preferred embodiment, the second preparation quality test measures the nuclear stain density of the reference cells detected on the normal, successfully processed, slides. Measurements are stored in a "mean stain" bin. The mean optical density for each detected intermediate cell nucleus is calculated. Data for all the detected intermediate cell nuclei on the slide is accumulated in a 10-bin histogram. The average staining score for the normal slides is calculated. In the preferred embodiment, if the average staining score is greater than 4.2 and less than 6.4, the slide set passes the test; otherwise, the slide set fails.

In the preferred embodiment, the third preparation quality test counts the number of potentially abnormal cell nuclei detected on slides that process successfully (stage 3 abnormals). The 80th percentile of the normal slides which contain endocervical component cells is calculated. In the preferred embodiment, if the 80th percentile is greater than 3, the slide set passes the test; otherwise, the slide set fails.

In the preferred embodiment, the fourth preparation quality test measures the 80th percentile of the QC score of successfully processed normal slides which contain endocervical component cells is calculated. In the preferred embodiment, if the 80th percentile is greater than 0.15 and less than 0.6, the slide set passes the test; otherwise, the slide set fails.

In the preferred embodiment, the fifth preparation quality test measures the median of reference cell nuclear texture (nuclear blur average) for successfully processed normal slides which contain endocervical component cells. In the preferred embodiment, if the median is greater than 5.65, the slide set passes the test; otherwise, the slide set fails.

In step 70, the automated system performs a Classification Test. The Classification Test evaluates whether the customer slide and cell presentation are within the training range of the AutoPap® 300 System to enable an effective interpretation by the system. The test evaluates the accuracy of slide classifications for slides that are successfully processed.

The system accuracy test evaluates sensitivity to abnormal specimen morphology. The 80th percentile of the QC score of the normal slides is calculated. In the preferred embodiment, if more than 70% of the low grade slides and 80% of the high grade slides have QC scores above the 80th percentile for normal slides, the slide set passes the test; otherwise, the slide set fails.

In step 80, the automated system then integrates the results from the tests in steps 30–70. In some aspects of the invention, the tests may be weighted. For example, tests that affect accuracy may be given greater weight than tests that affect yield. For example, the physical characteristic test relates to yield rather than accuracy and would be given less weight. In the preferred embodiment, the slide set must pass each test or the slide set is considered to fail. If the slide set passes, the test result integration in states that the slide set is acceptable in step 90. If the slide set fails, the test result integration makes recommendations for adjustment of the laboratory or clinic process in step 100.

Figure 3B:
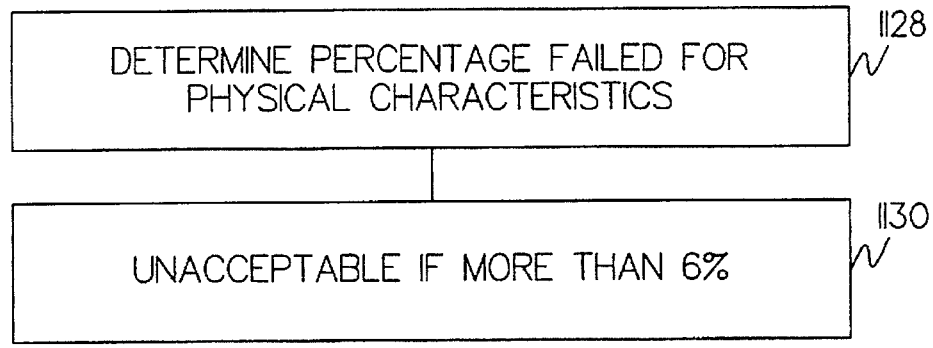

Now referring jointly to FIGS. 3A, 3B, 3C, 3D and 3E, FIG. 3A shows a more detailed flow chart of a method for assessing slide and specimen preparation quality. In one embodiment of the invention slides are collected at step 1102. At process step 1104 the collected slides are cleaned and a barcode is affixed to the slides. At process step 1106 the slides are processed in accordance with the various quality control methods described herein. Processing includes process steps 1108 through process step 1168 as shown in FIGS. 3A–3E and as described with reference to the tables hereinbelow. As best shown in FIG. 3B process step 1108 comprises process steps 1128, 1130. At process step 1128 a percentage of slides is determined as failing quality control processing for physical characteristics. At process step 1130 slides are determined to be unacceptable as failing quality control processing for physical characteristics if more than 6% of the slides failed this test.

Figure 3C:
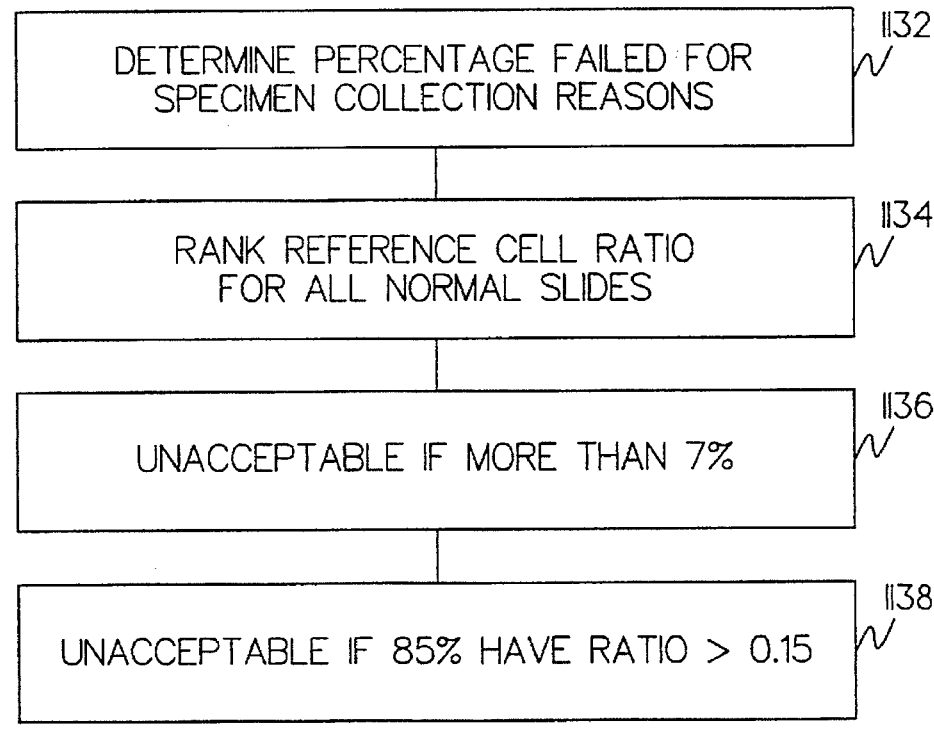

Referring now to FIG. 3C, a more detailed flow diagram of process step 1110 is shown. At process step 1132 a percentage of slides is determined as failing quality control processing for specimen collection characteristics. At process step 1134 reference cell ratios are ranked for all normal slides. At process step 1136 slides are determined to be unacceptable as failing quality control processing for specimen collection characteristics if more than 7% of the slides failed the specimen collection test. At process step 1138, slides are determined to be unacceptable if 85% of the slides have a reference cell ratio >0.15.

Figure 3D:
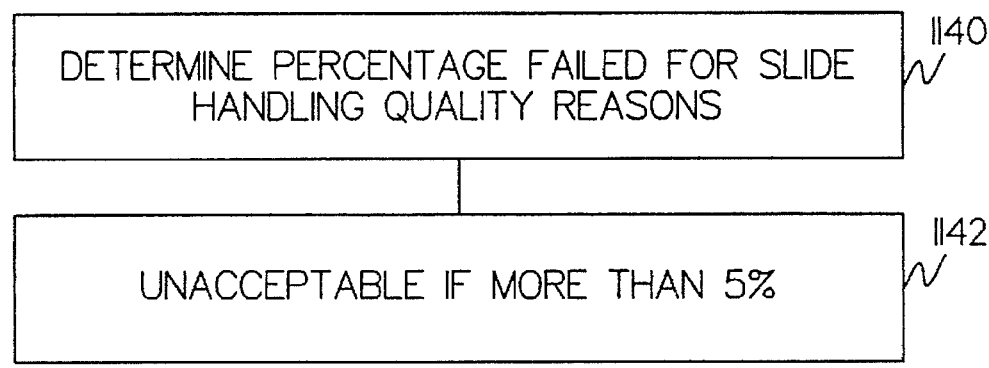

Referring now to FIG. 3D, a more detailed flow diagram of process step 1112 is shown. At process step 1140 a percentage of slides is determined as failing quality control processing for slide handling quality characteristics. At process step 1142 slides are determined to be unacceptable as failing quality control processing for slide handling quality characteristics if more than 5% of the slides failed this test.

Figure 3E:
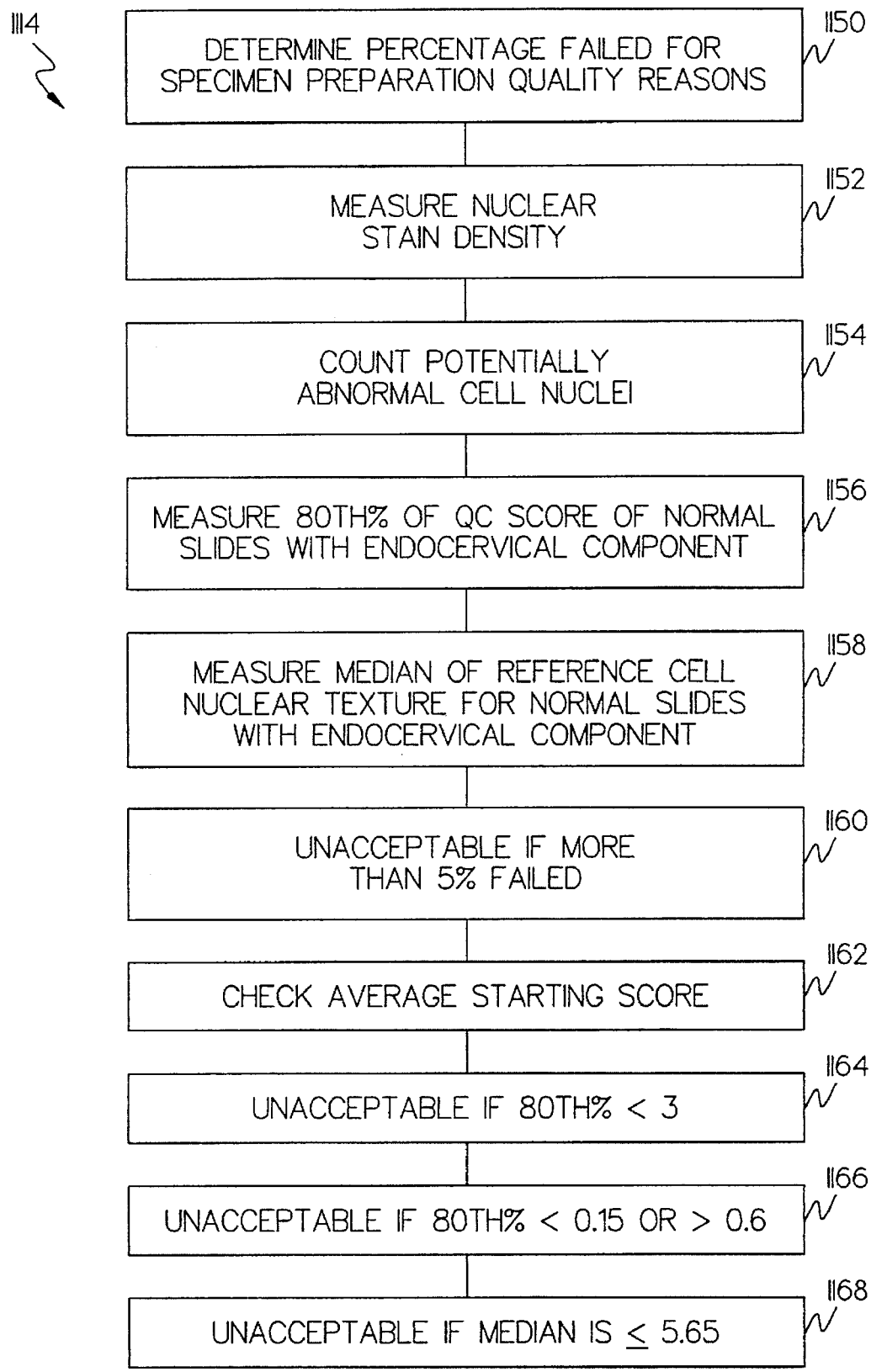

Referring now to FIG. 3E, a more detailed flow diagram of process step 1114 is shown. At process step 1150 a percentage of slides is determined as failing quality control processing for specimen preparation characteristics. At process step 1152 nuclear stain density of reference cells detected on slides is measured. At process step 1154 potentially abnormal cell nuclei on each slide are counted. At process step 1156 the 80th percentile of QC scores of normal slides with endocervical component is measured. At process step 1158 the median of reference cell nuclear texture for normal slides with endocervical component is measured. At process step 1160 slides are determined to be unacceptable as failing quality control processing for specimen quality characteristics if more than 5% of the slides failed this test. At process step 1162 the average starting score is checked. If the average starting score is less than 4.2 or greater than 6.4, the slides are deemed unacceptable for specimen preparation quality characteristics. At process step 1164, if the 80th percentile is less than 3 then the slides are not acceptable for specimen preparation quality characteristics. At process step 1166, if the 80th percentile is less than 0.15 or greater than 0.6 then the slides are not acceptable for specimen preparation quality characteristics. At process step 1168, if the median of reference cell nuclear texture for normal slides with an endocervical component is less than or equal to 5.65 then the slides are not acceptable for specimen preparation quality characteristics.

Referring again to FIG. 3A, at process step 1116 a percentage of abnormal slides is determined as scoring higher than the 80th percentile of normal specimens. At process step 1126 slides are determined to be not acceptable if fewer than 70% of the low grade slides or fewer than 80% of the high grade slides have scores higher than the 80th percentile of normal specimens.

Laboratory Process Monitoring Components

Figure 4:
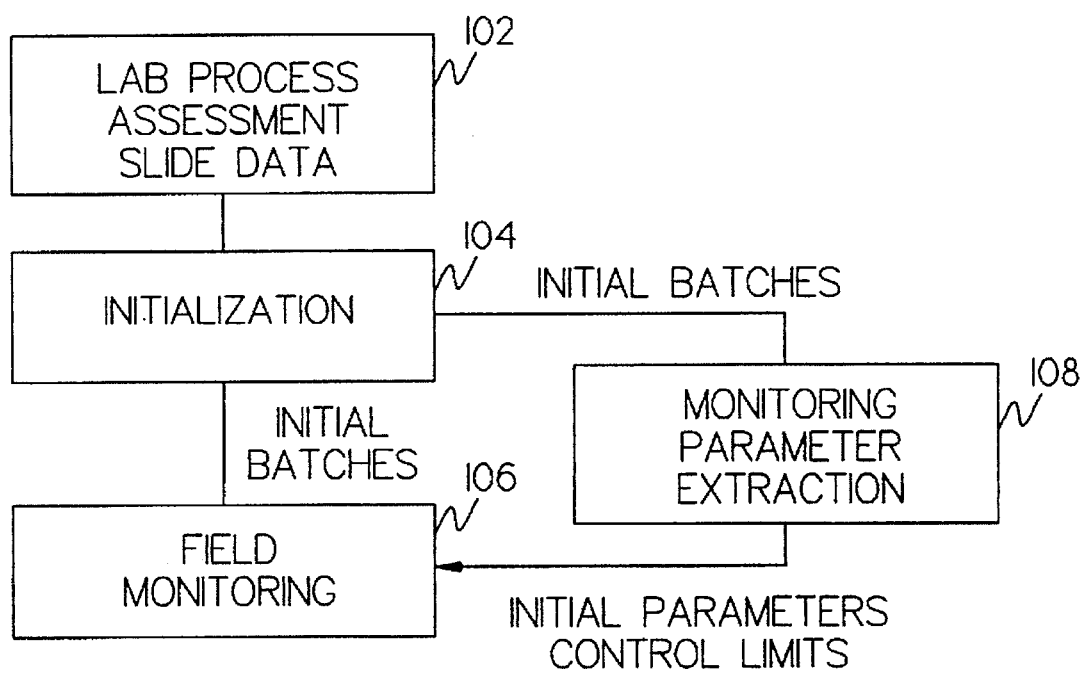
FIG. 4 shows a block diagram of one example of an initialization process for a laboratory process monitoring method and apparatus as employed in one embodiment of the invention.

Referring now to FIG. 4, FIG. 4 shows a block diagram of one example of an initialization process for a laboratory process monitoring method and apparatus as employed in one embodiment of the invention. In a preferred embodiment of implementation, the initialization process comprises an initialization module 104, a field monitoring module 106 and a monitoring parameter extraction module 108.

The initialization module 104 uses the lab process assessment slide data 102 acquired during the laboratory process assessment (LPA) to form an initial batch and characterization batch of slides. The monitoring parameter extraction module extracts the initial parameters, which determine the control limits of the monitoring parameters.

Initialization

Figure 8:
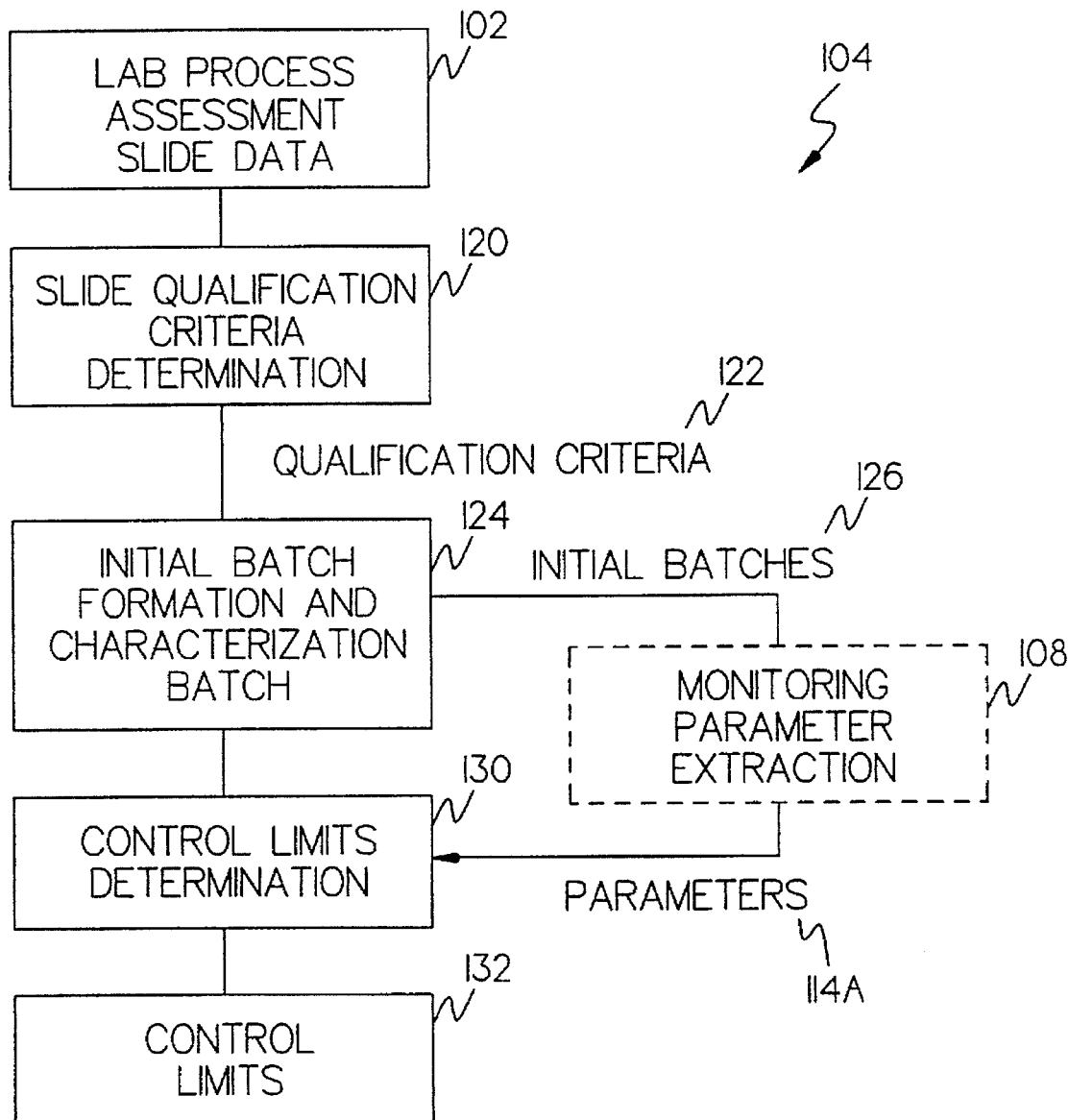
FIG. 8 shows a process flow diagram of one example of an initialization module as employed in one embodiment of the invention.

Referring now to FIG. 8, FIG. 8 shows a process flow diagram of one example of an initialization module 104 as employed in one embodiment of the invention. The initialization module 104 comprises a plurality of stages including a slide qualification criteria determination stage 120, an initial batch formation stage 124, and a control limits determination stage 130.

During Initialization, slide qualification criteria 120 are defined using the lab process assessment slide data 102 from the LPA. These criteria are then used to qualify slides and form the initial slide batch and characterization slide batch at process flow branch 126. Initial monitoring parameters 114A are extracted from the initial slide batch and characterization slide batch. Finally, the initial monitoring parameters 114A may be processed by the control limits determination stage 130 to define control limits 132 for monitoring the parameters.

Slide Qualification Criteria Determination

To ensure that the laboratory process assessment slides are representative of a particular laboratory's slide population, criteria may be established to qualify slides. At least two sets of criteria may be used for qualification including reduced process suitability limits and a global Qc score upper bound for slides that are successfully processed.

The reduced process suitability limits may be generated by adjusting the limits of the features used in suitability tests that determine the reliability of other slide scores. The adjustment is applied only to feature limits that are not exceeded by the feature values of the Laboratory Process Assessment slide data 102. Adjusted limits may be defined as the average of the original limit and the closest feature value of the LPA slide data 102.

The global Qc score upper bound may advantageously be determined using all the successfully processed normal slides in the Laboratory Process Assessment set. The slides are ranked by their Qc scores, and the Qc score value corresponding to the 90% quantile of the ranked distribution defines the global Qc score upper bound.

Initial Batch and Characterization Batch Formation

The initial batch for the AutoPap 300 System includes all normal slides in the Laboratory Process Assessment set. The initial batch further comprises a 3% random sample of the LSIL slides and a 4% random sample of the HSIL slides in the Laboratory Process Assessment set. Some monitoring parameters such as certain slide physical characteristic parameters are derived from the initial batch.

A preliminary characterization batch is formed from the initial batch by including only the slides that are successfully processed and have features within the reduced process suitability limits and Qc scores less than or equal to the global Qc score upper bound. A characterization batch is formed by excluding the slides that have Qc scores in the top and bottom 10% of the preliminary characterization slide batch. Some monitoring parameters, such as certain preparation parameters, are derived from the characterization batch.

Monitoring Parameter Extraction

During the initialization process, the monitoring parameter extraction module 108 extracts initial parameters that define the control limits 132 for the monitoring parameters. During the field monitoring process, the monitoring parameter extraction module 108 extracts monitoring parameters 114 from updated slide batches. Initial slide and characterization batches determine the initial monitoring parameters, which determine the initial control limits. The monitoring parameters 114 extracted from updated batches, falling within or outside the control limits 132, determine the compatibility of laboratory processes. Certain monitoring parameters, such as preparation monitoring parameters, are used to adjust or maintain staining and coverslipping processes.

The parameters used to monitor laboratory processes include slide physical characteristics parameters, specimen collection monitoring parameters, slide handling monitoring parameters, and preparation monitoring parameters.

Note that the reduced process suitability limits rather than the original process suitability limits are used for parameters, such as preparation monitoring parameters, throughout the parameter extraction process.

Slide-Physical Characteristics Parameters

The slide physical characteristics parameters monitor the physical characteristics of the slides processed by a laboratory. The slide physical characteristics parameters fall into general categories including slide characteristics, coverslip dimensional characteristics, and combined coverslip and specimen characteristics. Slides in a given batch are tested using set up or scanning failure conditions for each slide physical characteristics category.

To derive the slide physical characteristics parameters, the proportions of slides in a given batch that fail any of the tests are measured. The following proportions are output as slide physical characteristics parameters:

| P_slide | Slide characteristics failure proportion, |
| P_cover | Coverslip dimensional characteristics failure proportion, |
| P_cover/spec | Coverslip/specimen characteristics failure proportion, and |
| P_physical | overall slide physical characteristics failure proportion, | where P_physical=P_slide+P_cover+P_cover/spec.

Specimen Collection Monitoring Parameters

Figure 6:
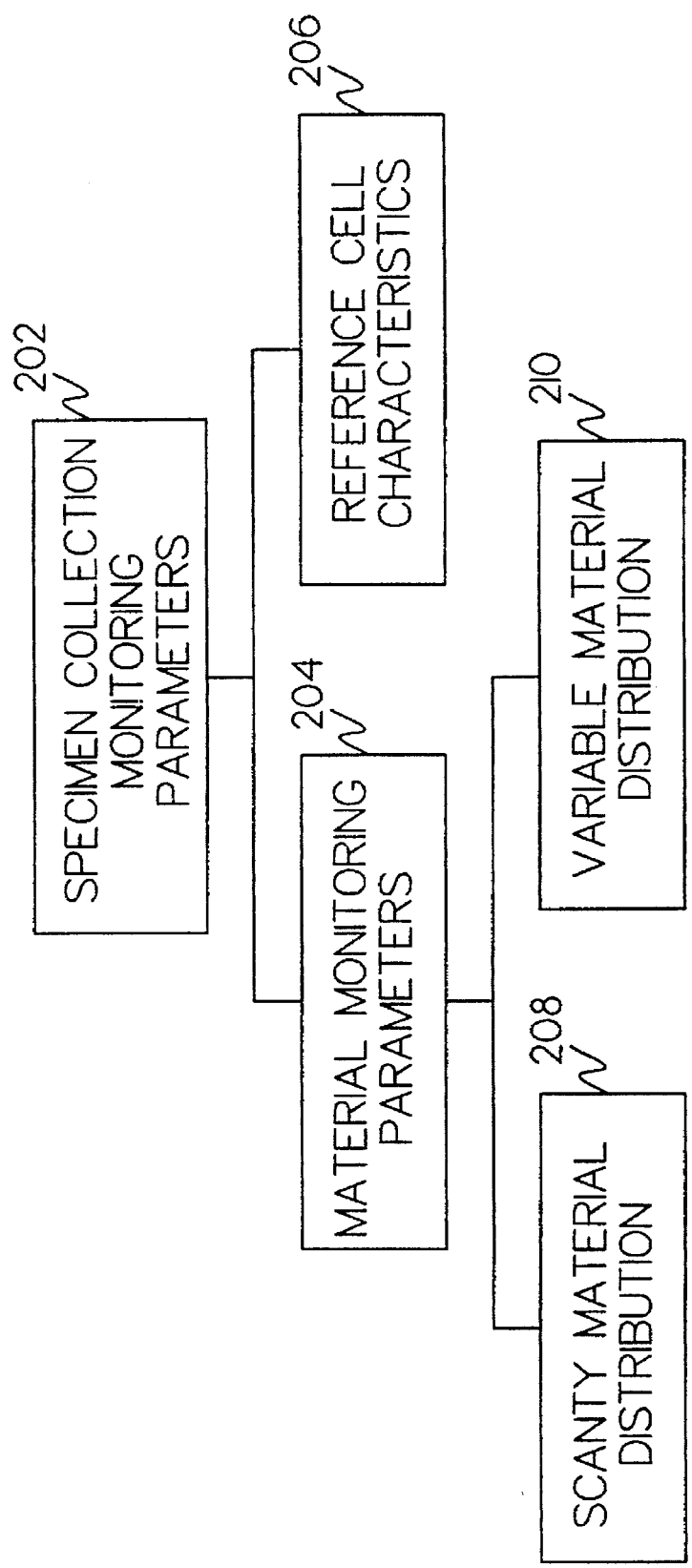
FIG. 6 shows sub-categories of specimen collection monitoring parameters as employed in one embodiment of the invention.

The specimen collection monitoring parameters 202 monitor the quality and sufficiency of the material of the collected cervical specimen for a given batch. As shown in FIG. 6, the specimen collection monitoring parameters 202 fall into categories including material monitoring parameters 204 and reference cell characteristics 206. The material monitoring parameters 204 further comprise a scanty material distribution parameter 208 and a variable material distribution parameter 210.

Material Monitoring Parameters

Slides in a given batch of slides are tested using set up, scanning and process suitability failure conditions for each material monitoring parameter category. The proportions of slides in the batch failing any of the material quality tests are measured as the material monitoring parameters.

Reference Cell Characteristics Parameter

The reference cell parameter is the 85% quantile of the number of reference cells divided by all detected objects derived from all the characterization-batch slides in the given slide batch.

Output Parameters

The following measurements are output as specimen collection monitoring parameters:

| P_scanty | scanty material distribution failure proportion, |
| P_variable | variable material distribution failure proportion, |
| P_material | overall material quality failure proportion, and |
| P_reference | reference cell characteristics parameter, | where P_material=P_scanty+P_variable.

Slide Handling Monitoring Parameters

The slide handling monitoring parameters monitor the quality of a customer's slide handling practices. The slide handling monitoring parameters fall into general categories including a barcode error, positioning error, and cleaning error.

Slides in a given batch are tested using scanning and process suitability failure conditions for each slide handling quality category. To derive the parameters, the proportions of slides in a given batch that fail any of the tests are measured. The following proportions are output as slide handling monitoring parameters:

| P_barcode | barcode error failure proportion, |
| P_position | positioning error failure proportion, |
| P_clean | cleaning error failure proportion, and |
| P_handling | overall slide handling quality failure proportion, | where P_handling=P_barcode+P_position+P_clean.

Slide Preparation Monitoring Parameters

Figure 7:
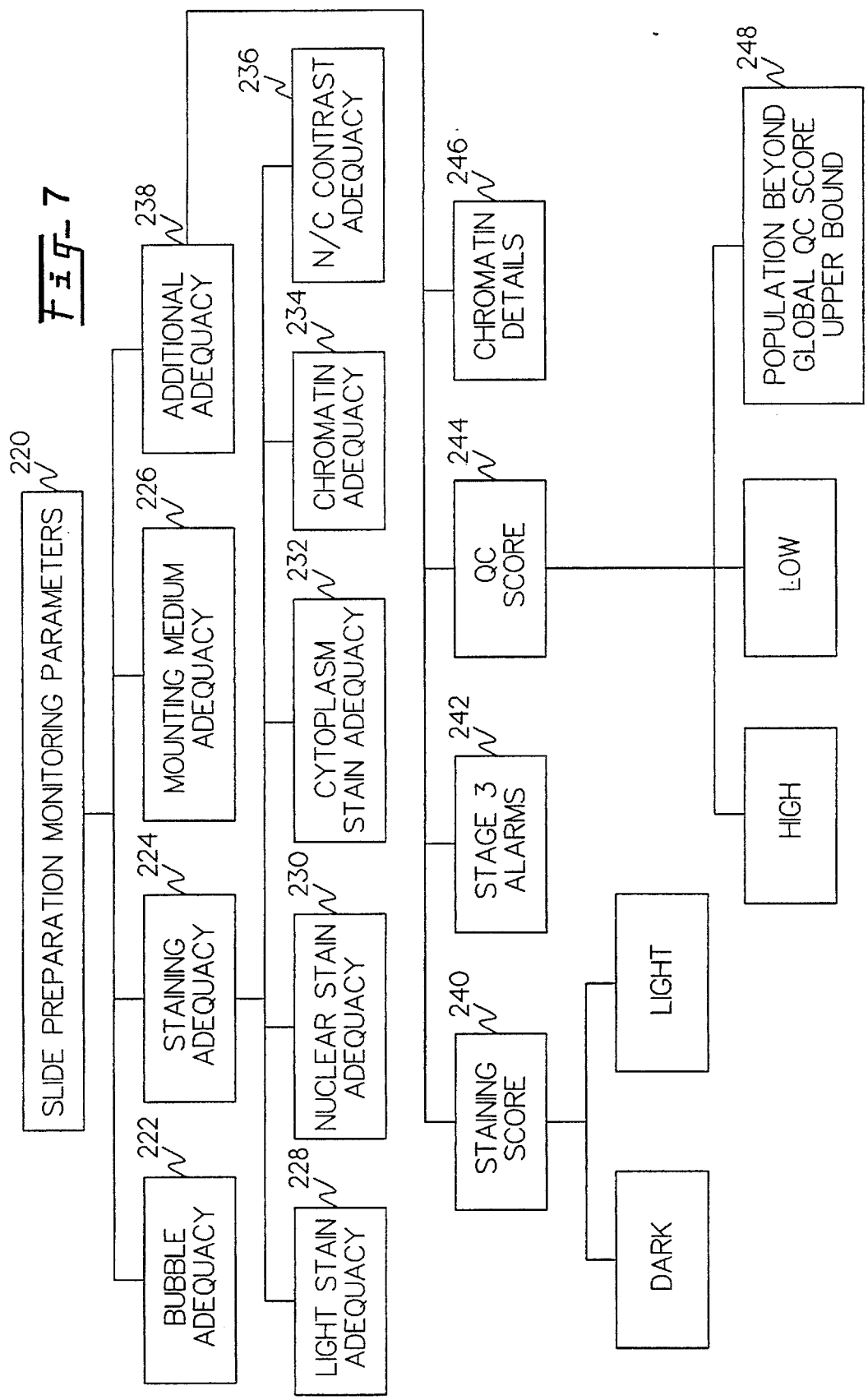
FIG. 7 shows categories of preparation monitoring parameters as employed in one embodiment of the invention.

The slide preparation monitoring parameters monitor the quality of a laboratory's fixation, staining, and coverslip application processes. As shown in FIG. 7, the preparation monitoring parameters may advantageously comprise:

bubble adequacy 222, mounting medium adequacy 226, staining adequacy 224, and additional adequacy 238.

In addition, the staining adequacy 224 and additional adequacy 238 categories contain subcategories of parameters. Staining adequacy 224 may further include light stain adequacy 228, nuclear stain adequacy 230, cytoplasm stain adequacy 232, chromatin adequacy 234, and N/C contrast adequacy 236. Additional adequacy 238 may further include staining score adequacy 240, stage3 alarms 242, QC score 244, and chromatin details 246. The categories are defined in more detail below.

Bubble, Staining, and Mounting Medium Adequacy Parameters

Slides in a given batch are tested using scanning and process failure conditions for each category. The proportions of slides in a given slide batch failing one or more of the preparation quality tests are measured as preparation monitoring parameters.

Additional Adequacy Parameters

Staining Score 240—This parameter measures the average staining score for slides from the characterization batch of a given slide batch. Mean_stain_bin is the feature used for this measurement.

Stage 3 Alarm 242—This parameter measures the 80% quantile of the number of stage 3 alarms from all characterization-batch slides in a given slide batch.

QC Score 244—This parameter measures the maximum Qc score of all characterization-batch slides in a given slide batch.

Population beyond Global QC Score Upper Bound 248—This parameter measures the percentage of slides in a given slide batch having the Qc score values greater than the global Qc score upper bound (see Global QC Score Upper Bound, described previously). Only the slides within the scanning and reduced process suitability limits are measured.

Chromatin Details 246—This parameter measures the median value of nuclear texture (nuclear_blur_avg) for all characterization-batch slides in a given slide batch.

Output Parameters

The following measurements are output as slide preparation monitoring parameters:

| | |
|---|---|
| P_bubble | bubble adequacy failure proportion, |
| P_medium | mounting medium failure proportion, |
| P_light_stain | light stain failure proportion, |
| P_nuc_stain | nuclear stain failure proportion, |
| P_cyto_stain | cytoplasm stain failure proportion, |
| P_chromatin | chromatin adequacy failure proportion, |
| P_N/C_cntst | N/C contrast adequacy failure proportion, |
| P_staining | overall staining adequacy failure proportion, |
| P_preparation | combined bubble, mounting medium, and staining adequacy failure proportions, |
| P_SS | staining score parameter, |
| P_alarm3 | stage 3 alarm parameter, |
| P_QC | QC score parameter, |
| P_global | population beyond global QC score upper bound, and |
| P_detail | chromatin details parameter, | where P_staining=P_light_stain+P_nuc_stain+P_cyto_stain+P_chromatin+P_N/C_cntst.
P_preparation=P_bubble+P_medium+P_staining.

Field Monitoring

Figure 5:
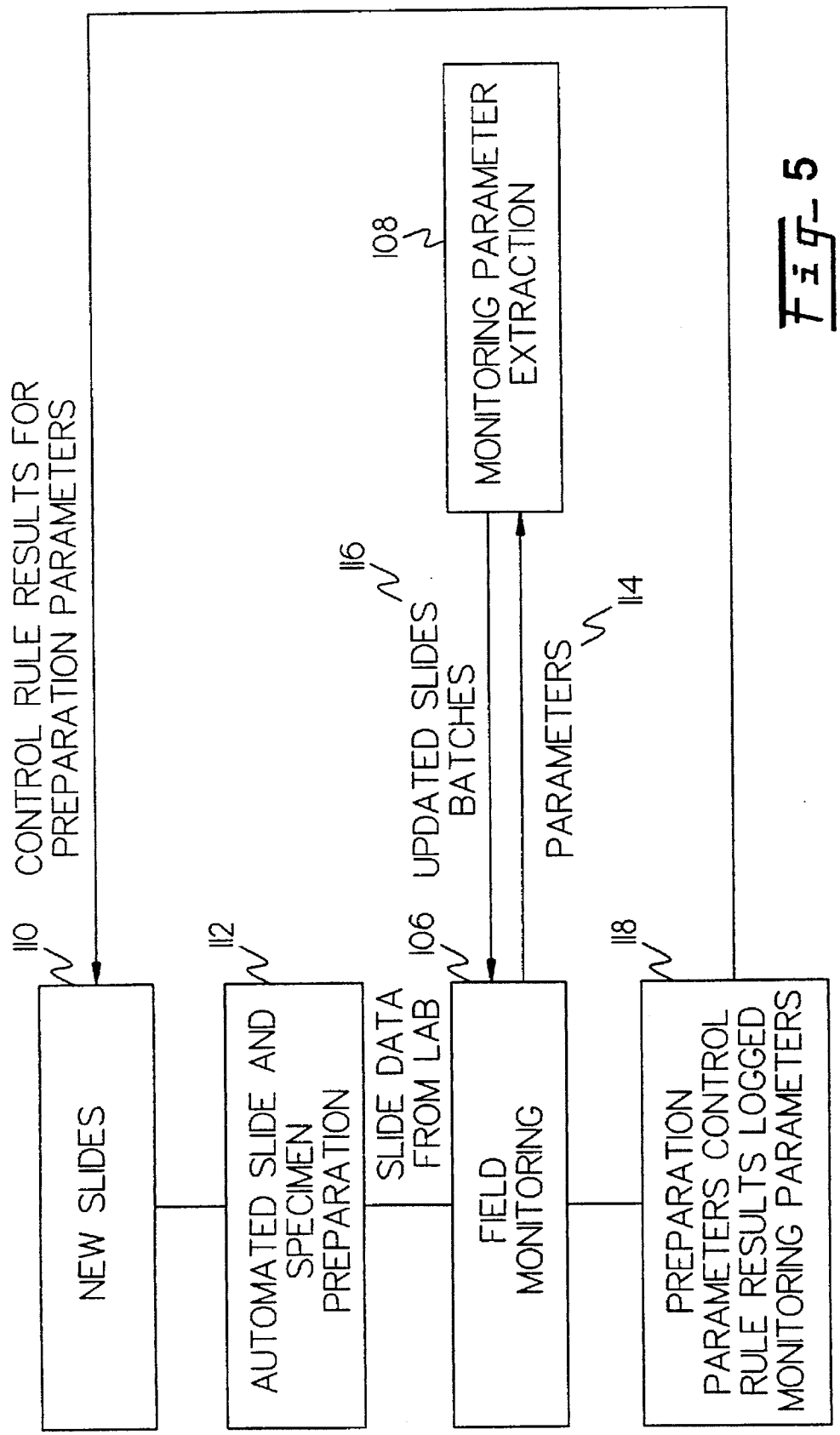
FIG. 5 shows a flow diagram of one example of a laboratory process monitoring method and apparatus as employed in one embodiment of the invention.

Referring now to FIG. 5, FIG. 5 shows a flow diagram of one example of a laboratory process monitoring method and apparatus as employed in one embodiment of the invention. An automated slide and specimen preparation module 112 controls the coverslip application and staining processes for new slides 110 using conventionally available automated instruments. Slides are considered to be new slides if they have not been previously assessed. The protocols for coverslip application and staining slide specimens used during the preparation of slides for the LPA determine the processes for applying coverslips and staining slide specimens for initial process monitoring. As field monitoring data becomes available, control rule results for preparation monitoring parameters are used to automatically maintain or adjust the processes for applying coverslips to slides and staining of slides.

The field monitoring module 106 dynamically updates a set of slide batches 116 and, using the monitoring parameter extraction module 108, the monitoring parameters are also dynamically updated. A plurality of extracted parameters 114 are compared with control limits to determine the integrity of the laboratory slide population and preparation processes. The control rule results for preparation parameters are used to automatically adjust slide and specimen preparation processes such as processes for using coverslips and staining.

Figure 9:
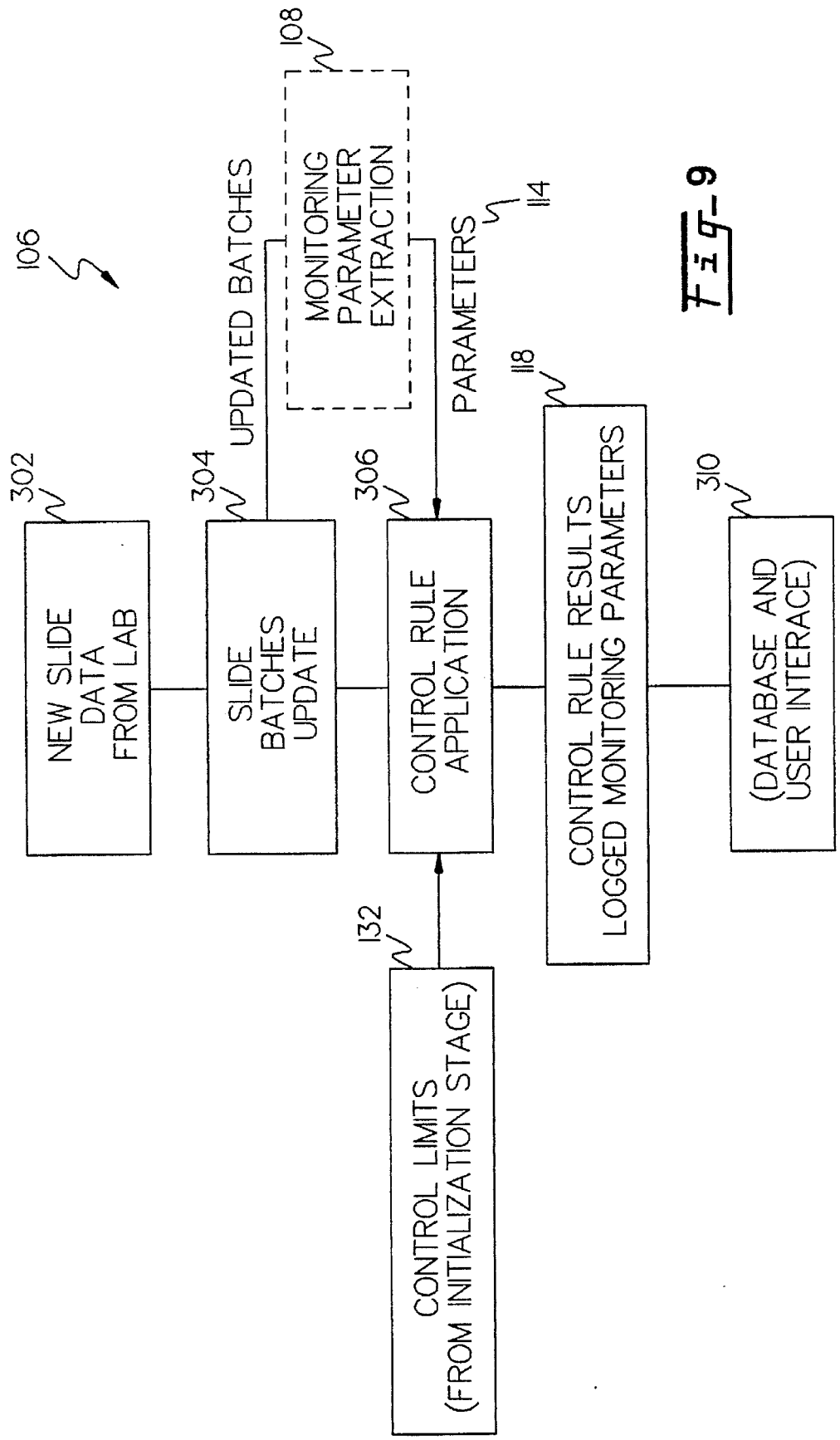
FIG. 9 shows a process flow diagram of one example of a field monitoring module as employed in one embodiment of the invention.

Referring now to FIG. 9, there shown is a process flow diagram of one example of a field monitoring module 106 as employed in one embodiment of the invention. The field monitoring module 106 may comprises two main stages in one example of the invention including a slide batches update stage 304 and a control limits determination stage.

During field monitoring, newly processed laboratory slide data 302 are used in the slide batches update stage 304 to update slide batches. The monitoring parameter extraction module 108 extracts parameters from the updated slide batches. The parameters 114 are used for the application of the control rules at control rule application stage 306. The control rule results and the logged monitoring parameters 118 are output to a product/service database and user interface module 310 so that the data can be displayed or printed in any suitable manner. Control rule results for certain preparation related parameters adjust and maintain staining and coverslip applying processes.

Slide Batches Update

During the field monitoring process, at least two batches may be continuously formed and updated including a short-term batch and a mid-term batch. The short-term batch includes up to 300 of the most recently processed laboratory slides. The mid-term batch is a superset of the mid-term batch and comprises up to 1,000 of the most recently processed slides. If the number of slides in a batch exceeds the batch limit, the oldest slides in the batch are removed to maintain the batch size to the upper limit.

The short-term batch is used to indicate recent (relative to the mid-term batch) variations in the laboratory process that can possibly be adjusted before causing severe process-related problems. The mid-term batch is used to apply the control rules. A laboratory process is considered "out of range" if the values of the monitoring parameters for the mid-term batch are outside of the control limits.

Monitoring Parameter Update

After the short-term and mid-term batches are updated, the short-term and mid-term batches are formed according to the rules specified in reference to the initialization module as described with reference to FIG. 9. The monitoring parameter extraction module 108 uses updated batches to extract the monitoring parameters.

Control Rule Applications

This section describes the control rules developed for the following monitoring parameters:

slide physical characteristics parameters,
specimen collection monitoring parameters,
slide handling monitoring parameters, and
preparation monitoring parameters.

The rules apply to only the slides in the mid-term batch. The laboratory process is considered "out of range" if any parameter falls outside the limits defined in the rules.

Slide Physical Characteristics Parameters P_physical

An upper limit is established for the overall slide physical characteristics failure proportion, P_physical. The upper limit is defined as:

P_physical Upper Limit=MAX(10%, 2*initial proportion of P_physical) where the initial proportion of P_physical is determined during the initialization stage based on the initial batch. If the P_physical of the mid-term batch is greater than the upper limit, the laboratory fails this monitoring test. The other parameters derived from slide physical characteristics such as P_slide, P_cover, and P_cover/spec are available as supporting evidence. They do not directly participate in the test.

Specimen Collection Monitoring parameters P_material

An upper limit is established for the overall material quality failure proportion, P_material. The upper limit is defined as:

P_material Upper Limit=MAX(10%, 2*initial proportion of P_material)

where the initial proportion of P_material is determined during the initialization stage based on the initial batch. If the P_material of the mid-term batch is greater than the upper limit, the laboratory fails this monitoring test.
P_reference In addition, a lower limit is established for the reference cell characteristics parameter, P_reference. The lower limit is defined as:

P_reference Lower Limit=MAX(0.01, initial proportion of P_reference /2)

where the initial proportion of P_reference is determined during the initialization stage based on the initial batch. If the P_reference of the mid-term batch is less than the lower limit, the laboratory fails this monitoring test. The other two specimen collection monitoring parameters: P_scanty and P_variable are available as supporting evidence. They do not directly participate in the test.

Slide Handling Monitoring parameters P_handling

An upper limit is established for the overall slide handling quality failure proportion, P_handling. The upper limit is defined as:

P_handling Upper Limit=MAX(8%, 2*initial proportion of P_handling)

where the initial proportion of P_handling is determined during the initialization stage based on the initial batch. If the P_handling of the mid-term batch is greater than the upper limit, the laboratory fails this monitoring test. The other three slide handling monitoring parameters: P_barcode, P_position, and P_clean are available as supporting evidence. They do not directly participate in the test.

Preparation Monitoring parameters P_preparation

An upper limit is established for the combined bubble, mounting medium, and staining adequacy failure proportion, P_preparation. The upper limit is defined as: P_preparation. Upper Limit=MAX(8%, 2*initial proportion of P_preparation) where the initial proportion of P_preparation is determined during the initialization stage based on the initial batch. If the P_preparation of the mid-term batch is greater than the upper limit, the laboratory fails this monitoring test.
P_SS In addition, two limits are established for the staining score parameter, P_SS. The lower limit is defined as:

P_SS Lower Limit=MAX(4.0, initial P_SS * 0.85)
The upper limit is defined as:

P_SS Upper Limit=MIN(6.6, initial P_SS * 1.15)
where the initial stain, P_SS, is determined during the initialization stage based on the initial batch. If the P_SS of the mid-term batch is less than the lower limit or greater than the upper limit, the laboratory fails this monitoring test.
P_alarm3

A lower limit is established for the stage 3 alarm parameter, P_alarm3. The lower limit is defined as:

P_alarm3 Lower Limit=MAX(3.0, initial P_alarm3 * 0.7)

where the initial P_alarm3 is determined during the initialization stage based on the initial batch. If the P_alarm3 of the mid-term batch is less than the lower limit, the laboratory fails this monitoring test.
P_QC Two limits are established for the Qc score parameter, P_QC. The lower limit is defined as:

P_QC Lower Limit=MAX(0.15, initial P_QC * 0.75)
The upper limit is defined as:

P_QC Upper Limit=MIN(0.6, initial P_QC * 1.25)
where the initial P_QC is determined during the initialization stage based on the initial batch. If the P_QC of the mid-term batch is less than the lower limit or greater than the upper limit, the laboratory fails this monitoring test.
P_detail A lower limit is established for the chromatin details parameter, P_detail. The upper limit is defined as:

P_detail Lower Limit=MAX(5.5, initial P_detail * 0.8)
where the initial proportion of P_detail is determined during the initialization stage based on the initial batch. If the P_detail of the mid-term batch is less than the lower limit, the laboratory fails this monitoring test.
P_global Lastly, two limits are established for the population beyond global Qc score upper bound parameter, P_global. The lower limit is defined as:

P_global Lower Limit=4%
and the upper limit is defined as:

P_global Upper Limit=20%

If the P_global of the mid-term batch is less than the lower limit or greater than the upper limit, the laboratory fails this monitoring test. The other preparation monitoring parameters, P_bubble, P_medium, P_light_stain, P_nuc_stain, P_cyto_stain, P_chromatin, P_N/C_cntst, and P_staining are available as supporting evidence. They do not directly participate in the test.

Figure 10:
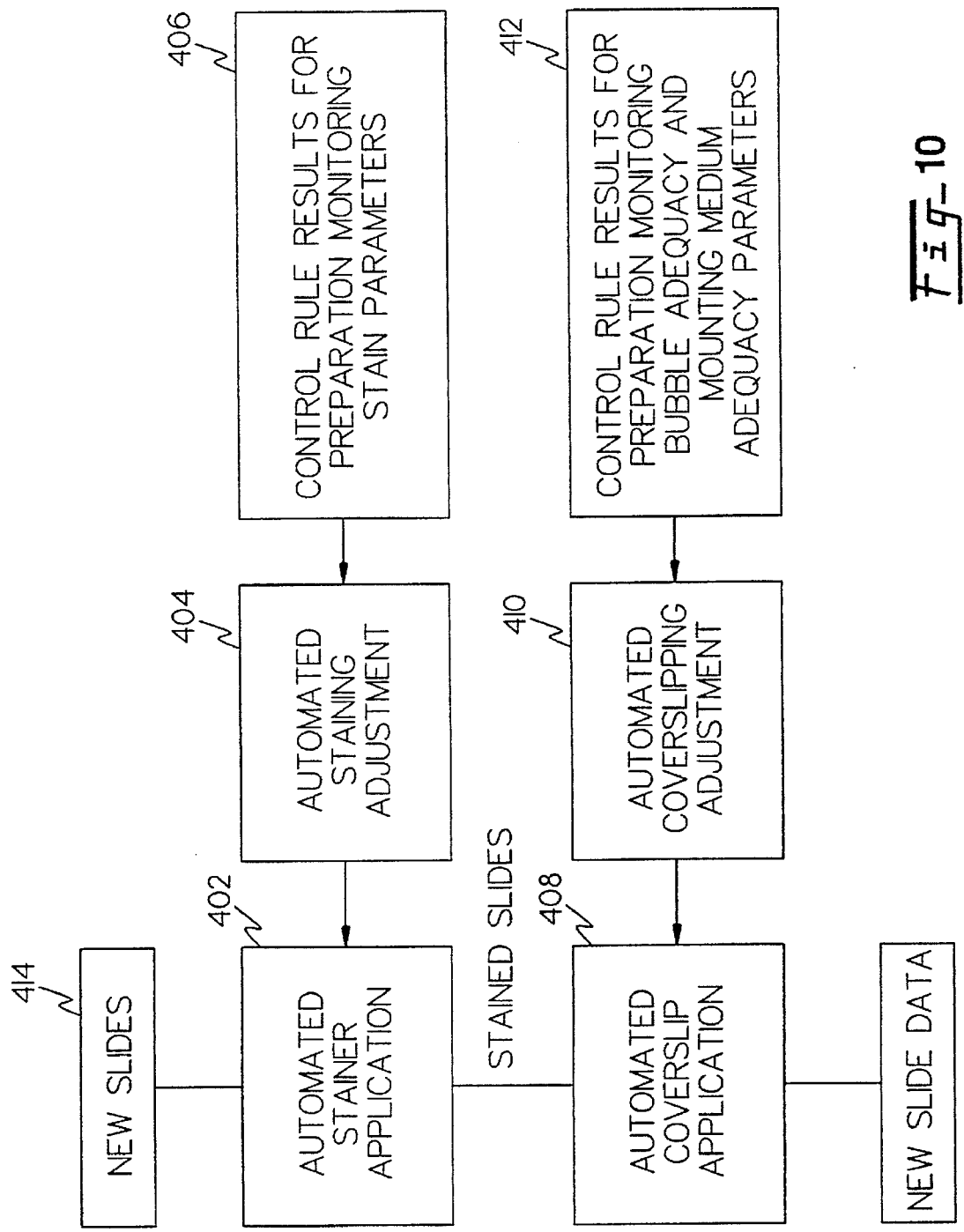
FIG. 10 shows a block diagram of one example of an automated slide and specimen preparation module as employed in one embodiment of the invention.

Referring now to FIG. 10, a block diagram of the automated slide and specimen preparation module as embodied in one example of the invention is there shown. The automated slide and specimen preparation module comprises an automated stainer application 402, an automated staining adjustment 404, an automated coverslip application 408 and an automated coverslip adjustment 410.

In operation, unstained slides without coverslips, here designated new slides 414, are input into the automated stainer application stage 402. In the automated stainer application stage 402 the protocol used during preparation of the LPA slide set determines the initial staining process used by the automated instrument. As field monitoring preparation parameters become available, the staining process is maintained or adjusted in an automated fashion using input obtained from the automated staining adjustment module.

In a similar fashion, staining processes may be adjusted at the automated staining adjustment stage 404 using control rules 406 derived from the data from preparation monitoring stain parameters. The adjustments are automatically applied to the automated stainer application 402.

Stained slides without coverslips are input into the automated coverslip application stage. The protocol used during preparation of the LPA slide set determines the initial coverslip application process for laboratory process monitoring. As field monitoring output becomes available, the coverslip application process is automatically maintained or adjusted using input obtained from the automated coverslip adjustment module.

In a similar fashion, coverslip application processes may be adjusted at the automated coverslip adjustment stage 410 responsive to control rules 412 derived from the data from preparation monitoring bubble parameters and mounting medium parameters. The adjustments are automatically applied to the automated stainer application.

The invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A laboratory process monitoring method for a laboratory that prepares slides said method comprising the steps of:

(a) acquiring an initial set of laboratory slides so as to select an initial batch of slides for initialization;

(b) extracting an initial monitor parameter with an automated cytology system from said initial batch of slides so as to determine a control limit;

(c) monitoring field data by extracting said monitor parameter from said field data with said automated cytology system; and (d) comparing said monitor parameter from said field data to said control limit to monitor a slide preparation.

2. The laboratory process monitoring method of claim 1 further comprising the step of controlling coverslip application wherein protocols for coverslip application processes are responsive to said monitor parameter.

3. The laboratory process monitoring method of claim 2 further comprising the steps of:

(a) acquiring field monitoring data; and (b) applying control rule results for at least one slide preparation monitor parameter to automatically regulate coverslip application.

4. The laboratory process monitoring method of claim 1 further comprising the step of controlling staining processes wherein protocols for staining application processes are responsive to said monitor parameter.

5. The laboratory process monitoring method of claim 4 further comprising the steps of:

(a) acquiring field monitoring data; and (b) applying control rule results for at least one slide preparation monitor parameter to automatically regulate staining of slides.

6. The laboratory process monitoring method of claim 1 wherein the step of monitoring field data further comprises the steps of:

(a) dynamically updating a set of slide batches;

(b) dynamically updating said monitor parameter using the updated slide batches to produce an updated monitor parameter; and (c) comparing said updated monitor parameter with said control limit to determine integrity of a laboratory slide population and at least one preparation process.

7. The laboratory process monitoring method of claim 6 further comprising the step of ruling a laboratory process out of range if said monitor parameter falls outside of said control limit.

8. The laboratory process monitoring method of claim 6 wherein the step of dynamically updating a set of slide batches further comprises the step of continuously forming and updating two batches including a short-term batch and a mid-term batch.

9. The laboratory process monitoring method of claim 8 wherein the short-term batch includes up to a first predetermined number of most recently processed laboratory slides.

10. The laboratory process monitoring method of claim 8 wherein the mid-term batch comprises a superset of the short-term batch and comprises up to a second predetermined number of most recently processed slides and wherein a laboratory process is considered "out of range" if values of monitoring parameters for the mid-term batch are outside control limits.

11. The laboratory process monitoring method of claim 8 wherein the step of continuously forming and updating two batches, including a short-term batch and a mid-term batch, further includes the step of reporting recent variations in laboratory process based on the short-term batch that can be adjusted before adverse screening conditions occur, thereby allowing tracking of variation patterns, and providing the means to forecast adverse conditions.

12. The laboratory process monitoring method of claim 1 wherein the step of acquiring an initial set of laboratory slides further comprises the steps of:

(a) determining slide qualification criteria using the initial set of laboratory slides; and (b) selecting an initial batch of slides using said initial set;

(c) forming a characterization batch using said initial batch of slides using said slide qualification criteria and (d) determining said control limit by extracting said initial monitor parameter from the initial batch of slides or characterization batch.

13. The laboratory process monitoring method of claim 12 wherein the step of determining slide qualification criteria further comprises the steps of:

(a) applying reduced process suitability limits; and (b) applying a global analysis score upper bound.

14. The laboratory process monitoring method of claim 13 wherein the step of applying reduced process suitability limits further comprises the steps of generating reduced process suitability limits by adjusting limits of features used in suitability tests that determine a reliability of other slide scores, wherein adjustment is applied only to feature limits that are not exceeded by feature values of slide data, and wherein adjusted limits comprise an average of an original limit and a closest feature value of slide data.

15. The laboratory process monitoring method of claim 13 wherein the step of applying a global analysis score upper bound further comprises the step of determining a global analysis score upper bound using successfully processed normal slides that are ranked by their analysis scores.

16. The laboratory process monitoring method of claim 1 wherein the step of extracting an initial monitor parameter further comprises the step of extracting at least one slide physical characteristics parameter for monitoring physical characteristics of slides.

17. The laboratory process monitoring method of claim 16 wherein the at least one slide physical characteristics parameter is selected from the group consisting of a slide characteristics category, coverslip dimensional characteristics category, and combined coverslip and specimen characteristics category.

18. The laboratory process monitoring method of claim 16 wherein the step of extracting an initial monitor parameter further comprises the step of testing slides in a given batch by scanning failure conditions for each slide physical characteristics category.

19. The laboratory process monitoring method of claim 18 wherein the step of testing slides in a given batch by scanning failure conditions further comprises the steps of:

(a) measuring the proportions of slides that fail any scanning failure conditions; and (b) outputting at least one proportion as a slide physical characteristics parameter, wherein the at least one proportion is selected from the group consisting of slide characteristics failure proportion, coverslip dimensional characteristics failure proportion, coverslip/specimen characteristics failure proportion, and overall slide physical characteristics failure proportion.

20. The laboratory process monitoring method of claim 1 wherein the step of extracting an initial monitor parameter further comprises the step of extracting at least one specimen collection monitoring parameter for monitoring quality or sufficiency of a collected specimen.

21. The laboratory process monitoring method of claim 20 wherein the at least one specimen collection monitoring parameter is selected from the group consisting of a material monitoring parameters category and reference cell characteristics category.

22. The laboratory process monitoring method of claim 21 wherein said material monitoring parameters category is selected from the group consisting of a scanty material distribution parameter and a variable material distribution parameter.

23. The laboratory process monitoring method of claim 21 wherein the reference cell characteristics category further comprises a predetermined percentage of the number of reference cells divided by all detected objects.

24. The laboratory process monitoring method of claim 20 wherein the step of extracting at least one specimen collection monitoring parameter further comprises the steps of:

(a) testing at least one slide specimen collection monitoring category by measuring the proportions of slides in a given batch that fail any scanning failure conditions or process suitability conditions; and (b) outputting at least one proportion as a specimen collection characteristic parameter wherein the at least one proportion is selected from the group consisting of scanty material proportion, distribution failure proportion, variable material distribution failure proportion, and overall material quality failure proportion.

25. The laboratory process monitoring method of claim 1 wherein the step of extracting an initial monitor parameter further comprises the step of extracting at least one slide handling monitoring parameter for monitoring quality of a laboratory's slide handling practices.

26. The laboratory process monitoring method of claim 25 wherein the at least one slide handling monitoring parameter is selected from the group consisting of a barcode error category, a positioning error parameter category, and a cleaning error parameter category.

27. The laboratory process monitoring method of claim 26 wherein the step of extracting at least one slide handling monitoring parameter further comprises the steps of:

(a) testing at least one slide handling quality category by measuring the proportions of slides in a given batch that fail any scanning failure conditions or process suitability conditions; and (b) outputting at least one proportion as a slide handling monitor parameter wherein the at least one proportion is selected from the group consisting of barcode error failure proportion, positioning error failure proportion, cleaning error failure proportion, and overall slide handling quality failure proportion.

28. The laboratory process monitoring method of claim 1 wherein the step of extracting an initial monitor parameter further comprises the step of extracting at least one preparation monitoring parameter for monitoring the quality of a laboratory fixation, staining, or coverslip application processes.

29. The laboratory process monitoring method of claim 28 wherein the at least one preparation monitoring parameter is selected from the group consisting of a bubble adequacy category, a mounting medium adequacy category, a staining adequacy category, and an additional adequacy category.

30. The laboratory process monitoring method of claim 29 wherein the staining adequacy further comprises a light stain adequacy category, nuclear stain adequacy category, cytoplasm stain adequacy category, chromatin adequacy category, and N/C contrast adequacy category.

31. The laboratory process monitoring method of claim 29 wherein the additional adequacy category further comprises staining score adequacy category, stage3 alarm category, QC score category, and chromatin details category.

32. The laboratory process monitoring method of claim 29 wherein the step of extracting at least one preparation monitoring parameter further comprises the steps of:

(a) testing at least one preparation monitoring category by measuring the proportions of slides in a given batch that fail any scanning failure conditions or process suitability conditions; and (b) outputting at least one proportion as a preparation monitoring parameter wherein the at least one proportion is selected from the group consisting of bubble adequacy failure proportion, mounting medium failure proportion, light stain failure proportion, nuclear stain failure proportion, cytoplasm stain failure proportion, chromatin adequacy failure proportion, N/C contrast adequacy failure proportion, overall staining adequacy failure proportion, and combined bubble mounting, medium and staining adequacy failure proportion.

33. The laboratory process monitoring method of claim 29 wherein the step of extracting at least one preparation monitoring parameter further comprises the step of outputting at least one preparation monitoring parameter from the group consisting of a staining score parameter, a stage3 alarm parameter, a QC score parameter, a population beyond global QC score upper bound parameter and a chromatin details parameter.

* * * * *

UNITED STATES PATENT AND TRADEMARK OFFICE
CERTIFICATE OF CORRECTION

PATENT NO. : 5,625,706
DATED : April 29, 1997
INVENTOR(S) : Lee et al.

It is certified that error appears in the above-identified patent and that said Letters Patent is hereby corrected as shown below:

Column 3, line 32, delete the number "0,528,703" and replace it with -- 5,528,703 --.

Column 5, line 49, delete "evaluates" and replace it with -- evaluate --.

Column 5, Table 1, line 64 delete the word "with" and replace it -- within --.

Column 10, line 42, delete the word "Qc" and replace it with -- QC --.

Column 10, line 52, delete the word "Qc" and replace it with -- QC --.

Column 10, line 55, delete both occurrences of the word "Qc" and replace them with -- QC --.

Column 10, line 57, delete the word "Qc" and replace it with -- QC --.

Column 11, line 2, delete the word "Qc" and replace it with -- QC --.

Column 11, line 3, delete the word "Qc" and replace it with -- QC --.

Column 11, line 4, delete the word "Qc" and replace it with -- QC --.

UNITED STATES PATENT AND TRADEMARK OFFICE
CERTIFICATE OF CORRECTION

PATENT NO. : 5,625,706
DATED : April 29, 1997
INVENTOR(S) : Lee et al.

It is certified that error appears in the above-identified patent and that said Letters Patent is hereby corrected as shown below:

Column 13, line 15, delete the word "Qc" and replace it with -- QC --.

Column 13, line 19, delete the word "Qc" and replace it with -- QC --.

Column 13, line 20, delete the word "Qc" and replace it with -- QC --.

Column 13, line 49, delete "N/C_$_{cntst}$" and replace it with -- N/C_cntst --.

Column 13, line 50, delete "$p$_preparation" and replace it with -- P_preparation --.

Column 14, line 14, delete "comprises" and replace it with -- comprise --.

Column 16, line 29, delete "Qc" and replace it with -- QC --.

Signed and Sealed this

Eighth Day of September, 1998

Attest:

BRUCE LEHMAN

*Attesting Officer*    *Commissioner of Patents and Trademarks*